(12) United States Patent
Bhatia et al.

(10) Patent No.: US 12,106,510 B2
(45) Date of Patent: Oct. 1, 2024

(54) METHOD AND SYSTEM FOR DETECTING LANDMARKS IN MEDICAL IMAGES

(71) Applicant: Siemens Healthcare GmbH, Erlangen (DE)

(72) Inventors: Parmeet Bhatia, Paoli, PA (US); Yimo Guo, Chester Springs, PA (US); Gerardo Hermosillo Valadez, West Chester, PA (US); Zhigang Peng, Ambler, PA (US); Yu Zhao, Athens, GA (US)

(73) Assignee: SIEMENS HEALTHINEERS AG, Forchheim (DE)

( * ) Notice: Subject to any disclaimer, the term of this patent is extended or adjusted under 35 U.S.C. 154(b) by 407 days.

(21) Appl. No.: 17/190,674

(22) Filed: Mar. 3, 2021

(65) Prior Publication Data

US 2021/0287363 A1 Sep. 16, 2021

(30) Foreign Application Priority Data

Mar. 12, 2020 (EP) .................................. 20162636

(51) Int. Cl.
*G06T 7/00* (2017.01)
*A61B 90/00* (2016.01)
(Continued)

(52) U.S. Cl.
CPC ................ *G06T 7/73* (2017.01); *A61B 90/36* (2016.02); *G06T 3/60* (2013.01); *G06T 7/0012* (2013.01);
(Continued)

(58) Field of Classification Search
CPC ........... G06T 7/73; G06T 3/60; G06T 7/0012; G06T 7/70; G06T 2207/30004;
(Continued)

(56) References Cited

U.S. PATENT DOCUMENTS 9,569,736 B1 * 2/2017 Ghesu .................... G06N 20/00
2011/0243386 A1 10/2011 Sofka et al.
(Continued)

OTHER PUBLICATIONS

Walid Abdullah AL et al.: "Actor-Critic Reinforcement Learning for Automatie Left Atrial Appendage Segmentation", 2018 IEEE International Conference On Bioinformatics and Biomedicine (BIBM), IEEE, Dec. 3, 2018 , pp. 609-612, XP033507789.
(Continued)

*Primary Examiner* — Wesley J Tucker
*Assistant Examiner* — Han Hoang
(74) *Attorney, Agent, or Firm* — Harness, Dickey & Pierce, P.L.C.

(57) ABSTRACT

Disclosed is a computer-implemented method for detecting one or more anatomic landmarks in medical image data. In an embodiment, the method includes receiving a medical image data set depicting a body part of a patient; and determining a first set of anatomic landmarks from a first representation of the medical image data set at a first resolution by applying a first trained function to the first representation of the medical image data set. Based on that, a second set of anatomic landmarks is determined from a second representation of the medical image data set at a second resolution, the second resolution being higher than the first resolution, by applying a second trained function different than the first trained function to the second representation of the medical image data set and using the first set of landmarks by the second trained function.

21 Claims, 8 Drawing Sheets

(51) Int. Cl.
  *G06T 3/60* (2006.01)
  *G06T 7/70* (2017.01)
  *G06T 7/73* (2017.01)
  *G06V 10/22* (2022.01)
  *G06V 10/40* (2022.01)
  *G06V 10/82* (2022.01)
  *G06V 30/24* (2022.01)

(52) U.S. Cl.
  CPC ............... *G06T 7/70* (2017.01); *G06V 10/22* (2022.01); *G06V 10/40* (2022.01); *G06V 10/82* (2022.01); *G06V 30/2504* (2022.01); *A61B 2090/363* (2016.02); *G06T 2207/30004* (2013.01)

(58) Field of Classification Search
  CPC .......... G06T 2207/10072; G06T 2207/10116; G06T 2207/20016; G06T 2207/20081; G06T 2207/20084; A61B 90/36; A61B 2090/363; G06V 10/22; G06V 10/40; G06V 10/82; G06V 30/2504; G06V 2201/031
  See application file for complete search history.

(56) References Cited

U.S. PATENT DOCUMENTS

2017/0116497 A1* 4/2017 Georgescu ............. G06N 3/006
2017/0330319 A1* 11/2017 Xu ....................... A61B 5/4887
2023/0027978 A1* 1/2023 Gaborit .................. G16H 50/20

OTHER PUBLICATIONS

Walid Abdullah AL et al.: "Partial Policy-based Reinforcement Learning for Anatomical Landmark Localization in 3D Medical Images", Arxiv.org, Dec. 31, 2018, XP080998396, Retrieved from the Internet: URL:https://arxiv.org/pdf/1807.02908.pdf.
Florin-Cristian Ghesu et al: "Multi-Scale Deep Reinforcement Learning for Real-Time 3D-Landmark Detection in CT Scans", IEEE Transactions On Pattern Analysis and Machine Intelligence, vol. 41, No. 1, Jan. 1, 2019, pp. 176-189, XP055725456.
European Search Report for European Application No. 20162636.3 dated Sep. 7, 2020.
Ronald J. Williams, "Simple statistical gradient-following algorithms for connectionist reinforcement learning", Machine learning 8.3-4, 1992, pp. 229-256.

* cited by examiner

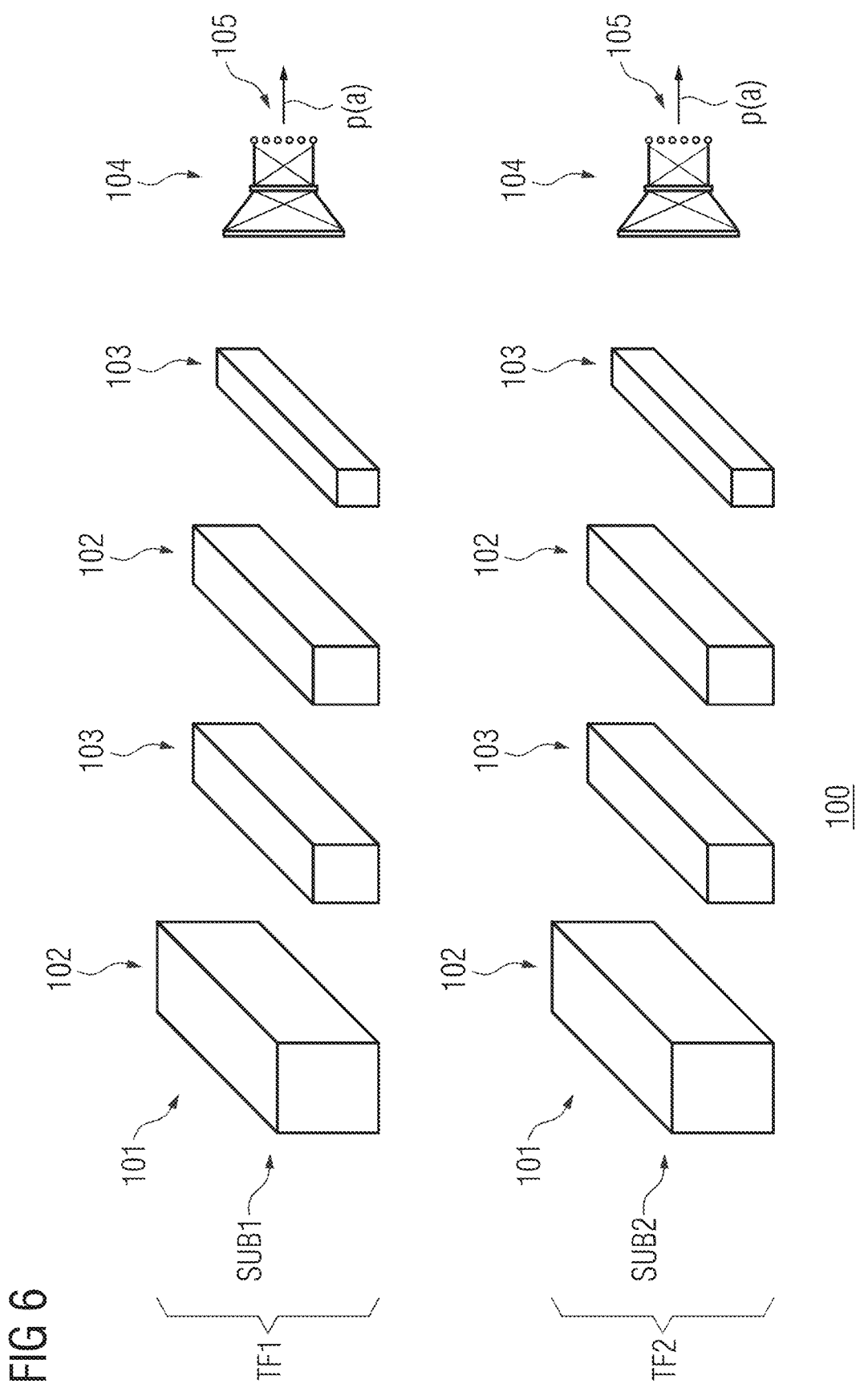

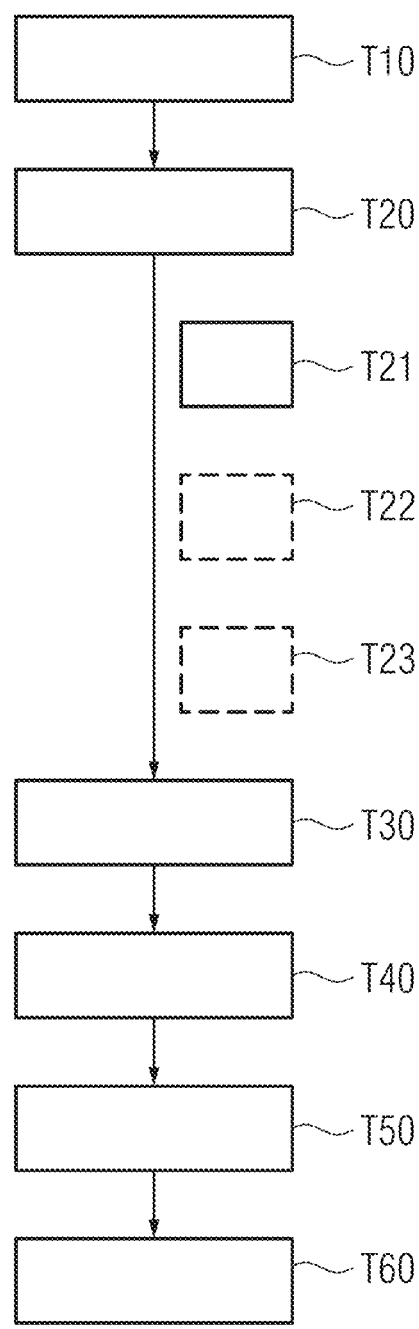

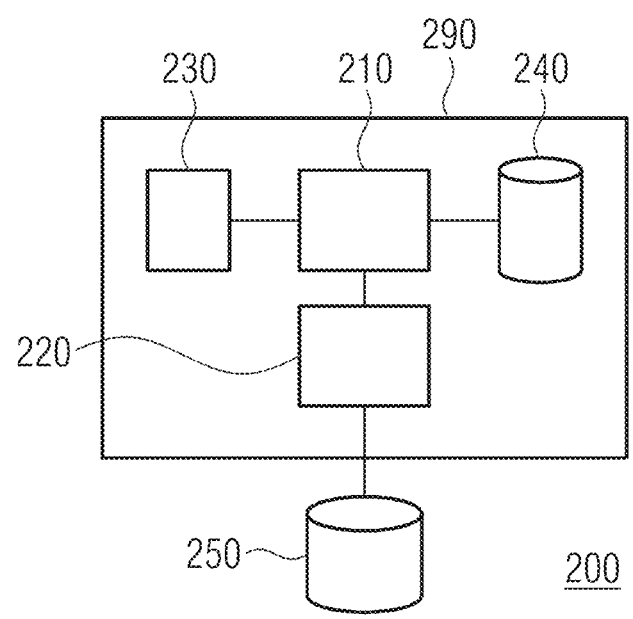

METHOD AND SYSTEM FOR DETECTING LANDMARKS IN MEDICAL IMAGES

PRIORITY STATEMENT

The present application hereby claims priority under 35 U.S.C. § 119 to European patent application number EP20162636.3 filed Mar. 12, 2020, the entire contents of which are hereby incorporated herein by reference.

FIELD

Example embodiments of the present application generally relate to medical image processing, such as image processing for computed tomography images or magnetic resonance images, and, in particular, to the detection of anatomic landmarks in medical image data.

BACKGROUND

Accurate detection of anatomic landmarks is a fundamental prerequisite in medical image analysis. Landmarks are used in a plethora of steps in medical imaging workflows. These steps comprise disease diagnosis—either by a clinician or computer aided—alignment of medical image data, patient follow-up analysis, segmentation of anatomies, quantification of changes, comparing image data from different imaging modalities and so forth.

The automated detection of anatomic landmarks in medical image data is difficult due to the large amount of variations occurring between individual image studies. Variations comprise varying or partial fields of view, different viewing angles and image resolutions, as well as varying image quality amongst different medical imaging modalities.

In recent years, machine learning based techniques have been developed for automatically tracking and detecting anatomic landmarks in medical image data. These techniques are often based on feature learning and object recognition, where an intelligent agent is trained with image data comprising annotated landmarks in a supervised learning fashion. Typically, in these systems, the intelligent agent takes in the entire image at once and applies learned strategies to identify possible landmark locations.

SUMMARY

While suchlike approaches may work reasonably well under optimal circumstances, the inventors have discovered that traditional machine learned models have their limitations in less than optimal situations, e.g., if the training data is scarce or the image data to be analyzed is incomplete. Here, the search strategies followed by traditional machine learned models is often suboptimal and does not converge sufficiently well. By consequence, the automated landmark search may be perceived as unreliable and exhaustive by the user. What is more, most machine learned models are highly optimized for specific types of medical image data. While they work very well for images generated by a distinct imaging modality and having a distinct resolution, the inventors have discovered that they may underperform for differing parameter sets. The inventors have discovered that since there is the need in medical image reading and reporting to compare image data from very different modalities such as CT—with Ultrasound-data, the limited interoperability of existing methods poses a considerable disadvantage in practice.

Therefore, embodiments of the present invention provide a computer-implemented landmark detection tool and corresponding methods which support a user/physician/radiologist/pathologist in deriving a medical diagnosis from a medical image volume, in particular, by appropriately highlighting anatomic landmarks in medical image data. In particular, at least one embodiment of the present invention provides an improved computer-implemented method for robustly detecting anatomic landmarks and being applicable for a wide variety of input medical image data to directly support the user in clinical reading and reporting and increase the efficiency of clinical workflows.

Embodiments are directed to methods for detecting anatomic landmarks in medical image data, corresponding systems; a corresponding method for training an intelligent agent; a corresponding computer-program product and computer-readable storage medium. Alternative and/or preferred embodiments are subject of the claims.

In the following, the technical solution according to embodiments of the present invention is described with respect to the claimed apparatuses as well as with respect to the claimed methods. Features, advantages or alternative embodiments described herein can likewise be assigned to other claimed objects and vice versa. In other words, claims addressing at least one embodiment of the inventive method can be improved by features described or claimed with respect to at least one embodiment of the apparatuses. In this case, e.g., functional features of at least one embodiment of the method are embodied by objective units or elements of at least one embodiment of the apparatus.

According to an embodiment, a computer-implemented method for detecting one or more anatomic landmarks in medical image data is provided. The method comprises several steps. A first step is directed to receiving medical image data depicting a body part of a patient. In a next step, a first set of anatomic landmarks is determined from a first representation of the medical image data at a first resolution by applying a first trained function to the first representation of the medical image data. In a further step, a second set of anatomic landmarks is determined from a second representation of the medical image data at a second resolution, the second resolution being higher than the first resolution, by applying a second trained function to the second representation of the medical image data and using the first set of landmarks by the second trained function. Thereby, the second trained function is different from the first trained function.

According to a further embodiment, a method for building (assembling) an intelligent agent to determine anatomic landmarks in medical image data is provided. The method comprises several steps. A first step is directed to receiving a plurality of training medical image data sets respectively depicting the body part and comprising target landmark locations. A further step is directed to receiving first and second trained functions. A further step is directed to respectively generate at least first and second representations from the training medical image data sets, the first representations having a lower image resolution than the second representations. A further step comprises training the first trained function to identify anatomical landmarks at the first resolution by employing a scheme of iterative improvement of a predicted landmark location by defining a sub-space around the predicted landmark location in the first representation and reposition the sub-space in the first representation in one or more iterations following a learned policy by applying the first trained function to the first representations and using the target landmark locations to maximize a cumulative future reward value for a sequence of actions for repositioning the sub-space in the first representations. A further step comprises training the second trained function to identify anatomical landmarks at the second resolution by employing a scheme of iterative improvement of a predicted landmark location by defining a sub-space around the predicted landmark location in the second representation and reposition the sub-space in the second representation in one or more iterations following a learned policy by applying the second trained function to the second representations and using the target landmark locations to maximize a cumulative future reward value for a sequence of actions for repositioning the sub-space in the second representations. Yet a further step is directed to assembling the first trained function and the second trained function such that the second trained function inputs the output landmark locations of the first trained function as starting values.

According to another embodiment, the invention further relates to a training system for building (assembling) an intelligent agent. The system comprises an interface, embodied for receiving first and second trained functions, and further embodied for receiving the training medical image data sets. The training system further comprises a processor configured to carry out the method steps according to the above method for building (assembling) an intelligent agent.

According to an embodiment, a system for detecting one or more anatomic landmarks in medical image data is provided. The system comprises an interface unit for receiving a medical image data set depicting a body part of a patient, a memory storing a first trained function trained to identify a set of anatomic landmarks in a representation of the medical image data set at a first resolution, and a second trained function trained to identify a set of landmarks in a representation of the medical image data set at a second resolution higher than the first resolution. The system further comprises a computing unit configured to apply the first trained function to a first representation of the medical image data at the first resolution so as to identify a first set of anatomic landmarks, to input the first set of anatomic landmarks to the second trained function and to apply the second trained function to a second representation of the medical image data at the second resolution so as to identify a second set of anatomic landmarks using the first set of landmarks.

According to an embodiment, the system is adapted to implement the inventive method according to one or more of the aspects and embodiments as herein described before.

According to another embodiment, the invention further relates to an image analysis system comprising the system for detecting anatomic landmarks in medical image data and a medical image system configured to acquire, store and/or forward follow-up medical images (comprising the reference image data and the follow-up image data). Thereby, the interface unit may be configured to receive the medical image data from the medical image system.

According to another embodiment, the present invention is directed to a computer program product comprising program elements which induce a computing unit of a system for detecting anatomic landmarks in medical image data to perform the steps according to an embodiment of the above method, when the program elements are loaded into a memory of the computing unit.

According to another embodiment, the present invention is directed to a computer-readable medium on which program elements are stored that are readable and executable by a computing unit of a system for detecting anatomic landmarks in medical image data, in order to perform steps of an embodiment of the inventive method, when the program elements are executed by the computing unit.

The realization of an embodiment of the invention by a computer program product and/or a computer-readable medium has the advantage that already existing providing systems can be easily adopted by software updates in order to work as proposed by an embodiment of the invention.

The computer program product can be, for example, a computer program or comprise another element next to the computer program as such. This other element can be hardware, e.g., a memory device, on which the computer program is stored, a hardware key for using the computer program and the like, and/or software, e.g., a documentation or a software key for using the computer program. The computer program product may further comprise development material, a runtime system and/or databases or libraries. The computer program product may be distributed among several computer instances.

According to another embodiment, the present invention is directed to a computer-implemented method for detecting one or more anatomic landmarks in medical image data, comprising: receiving medical image data depicting a body part of a patient;

determining a first set of anatomic landmarks from a first representation of the medical image data at a first resolution by applying a first trained function to the first representation of the medical image data;

determining a second set of anatomic landmarks from a second representation of the medical image data at a second resolution, the second resolution being relatively higher than the first resolution, by applying a second trained function, different than the first trained function, to the second representation of the medical image data, the second trained function using the first set of anatomic landmarks.

According to another embodiment, the present invention is directed to a system for detecting one or more anatomic landmarks in medical image data, comprising:

an interface for receiving medical image data depicting a body part of a patient;

a memory storing a first trained function trained to identify a set of anatomic landmarks in a representation of the medical image data at a first resolution, and a second trained function different than the first trained function, and trained to identify a set of landmarks in a representation of the medical image data at a second resolution, relatively higher than the first resolution; and a processor configured to:
apply the first trained function to a first representation of the medical image data (MID) at the first resolution so as to identify a first set of anatomic landmarks;
input the first set of anatomic landmarks to the second trained function; and
apply the second trained function to a second representation of the medical image data at the second resolution, so as to identify a second set of anatomic landmarks using the first set of anatomic landmarks.

According to another embodiment, the present invention is directed to a non-transitory computer program product storing program elements, to induce a computing unit of a system for detecting one or more anatomic landmarks in medical image data to perform the method of an embodiment, when the program elements are loaded into a memory of, and executed by, the computing unit.

According to another embodiment, the present invention is directed to a non-transitory computer-readable medium storing program elements, readable and executable by a computing unit of a system for detecting one or more anatomic landmarks in medical image data, to perform the method of an embodiment when the program elements are executed by the computing unit.

BRIEF DESCRIPTION OF THE DRAWINGS

Characteristics, features and advantages of the above described invention, as well as the manner they are achieved, become clearer and more understandable in the light of the following description and embodiments, which will be described in detail with respect to the figures. This following description does not limit the invention on the contained embodiments. Same components or parts can be labeled with the same reference signs in different figures. In general, the figures are not drawn to scale. In the following:

FIG. 6 depicts an embodiment of an active agent based on first and second trained functions, FIG. 7 depicts a flowchart illustrating a method for training trained functions to detect one or more anatomic landmarks in medical image data according to an embodiment, and FIG. 8 shows a system for training trained functions to detect one or more anatomic landmarks in medical image data according to an embodiment.

DETAILED DESCRIPTION OF THE EXAMPLE EMBODIMENTS

Figure 1:
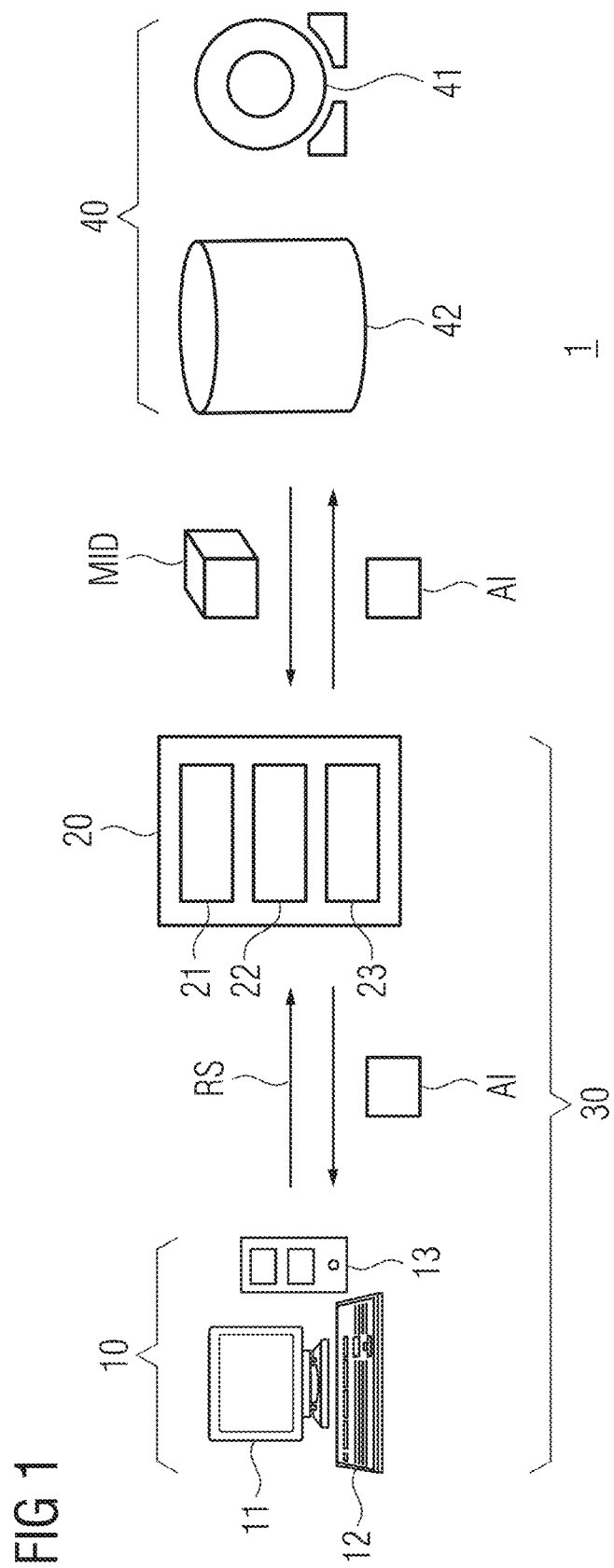
FIG. 1 depicts a system for detecting one or more anatomic landmarks in medical image data according to an embodiment.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. At least one embodiment of the present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature (s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without subdividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Bluray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Bluray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Nonlimiting examples of the non-transitory computer-readable medium include, but are not limited to, rewriteable nonvolatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable nonvolatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

According to an embodiment, a computer-implemented method for detecting one or more anatomic landmarks in medical image data is provided. The method comprises several steps. A first step is directed to receiving medical image data depicting a body part of a patient. In a next step, a first set of anatomic landmarks is determined from a first representation of the medical image data at a first resolution by applying a first trained function to the first representation of the medical image data. In a further step, a second set of anatomic landmarks is determined from a second representation of the medical image data at a second resolution, the second resolution being higher than the first resolution, by applying a second trained function to the second representation of the medical image data and using the first set of landmarks by the second trained function. Thereby, the second trained function is different from the first trained function.

The medical image data may relate to two-dimensional image data sets providing two dimensions in space. Further, the medical image data may relate to three-dimensional image data sets providing three dimensions in space. The medical image data depict a body part of a patient in the sense that it contains two- or three-dimensional image data of the patient's body part. The medical image data may, for example, be in the form of an array of pixels or voxels. Such arrays of pixels or voxels may be representative of intensity, absorption or other parameter as a function of three-dimensional position, and may, for example, be obtained by suitable processing of measurement signals obtained by a medical imaging modality. A medical imaging modality corresponds to a system used to generate or produce medical images. For example, a medical imaging modality may be a computed tomography system (CT system), a magnetic resonance system (MR system), an angiography (or C-arm X-ray) system, a positron-emission tomography system (PET system) or the like.

The depicted body part of the patient in general will comprise a plurality of anatomies and/or organs. Taking a chest image as an example, the medical image data may show lung tissue, the rib cage, lymph nodes and others. "Receiving" in the framework of the application may mean that the medical image data is acquired from the medical imaging modalities. Further receiving may mean that it is acquired from an appropriate memory such as a picture archiving and communication system (PACS) or any other suitable medical image storing facility. Further receiving may mean that the medical image data is received for further processing on a request base by a further computer-implemented algorithm.

First and second representations may generally relate to image data generated from the received medical image data sets. That is, first and second representations likewise relate to image data having a plurality of pixels or voxels. In general, first and second representations have the same dimensionality as the received medical image data—albeit with different image resolutions. The resolution may be an isotropic image resolution given in mm. The first representation may have a lower resolution than the medical image data. The second representation may likewise have a lower or the same resolution as compared to the medical image data.

Anatomic landmarks may relate to biological meaningful points, regions, contours, lines which are characteristic for anatomies comprised in a body part. In other words, anatomic landmarks relate to distinctive, measurable geometric identifiers definable in the depicted body part. Specifically, anatomic landmarks may be vertices, anchor points, control points, sites, profile points, 'sampling' points, nodes, markers, fiducial markers, points in a shape that are located according to some mathematical or geometrical property, fixed points, markers, features or structures that can be defined in the body part depicted in the medical image data. Although the locations of the anatomic landmarks are given in the coordinates of the underlying medical image data, their existence is invariant between individual medical image data sets and just depends on the underlying body part. Accordingly, anatomic landmarks can be used to register different image studies with one another or to describe the positional relationship of findings, observations, anatomies and organs inside the body parts independent of the subjective coordinate system spanned by the pixels or voxels of the medical image data set currently under investigation. In other words, the biometric data is at least to some extent universal in the sense that every body part of the same kind should possess the underlying trait.

Taking the chest area as an example, anatomic landmarks may be selected from the group comprising: aortic root and arch, artery bifurcations (the bifurcation of brachiocephalic, carotid or subclavian arteries, the celiac trunk, the renal bifurcation), carina bifurcation, the top of left and right kidney, top of left and right lung, center and top of the liver, pancreas, tip of the sternum, vertebral bodies. First and second sets of anatomic landmarks may comprise one or more (or all) landmarks comprised in the body part depicted in the medical image data. Further, first and second sets of landmarks may also comprise zero landmarks, if there are no anatomic landmarks comprised in the medical image data and/or if the trained functions were not able to detect any. In addition, first and second sets of landmarks may comprise different numbers of anatomic landmarks—a situation which may arise if one or more anatomic landmarks are only identifiable at the second resolution, or if a prospect landmark location outputted by the first trained function cannot be verified by the second trained function at the second resolution.

First and second trained functions, in general, may be seen as mapping input data to output data thereby fulfilling a certain learned task (in this case: detecting locations of anatomic landmarks in the respective representation at the corresponding resolution). The relation between input and output may be governed by one or more (in general: a plethora) of parameters embedded in the trained functions. The values of the parameters may be learned (adapted) during training according to the task, the trained function will have to fulfill. Other terms for trained function may be trained mapping specification, mapping specification with trained parameters, function with trained parameters, trained machine learned model, algorithm based on artificial intelligence, or machine learned algorithm.

Applying first and second trained functions may mean inputting information taken from the respective representation into the corresponding trained function. The output may be an indication of an anatomic landmark in the corresponding representation. The indication may comprise a landmark location (in terms of the coordinates of the landmark) and/or information as to the type of the detected landmark (e.g., in the form of a semantic descriptor). For fulfilling the learned task, the trained function may be trained using ground truth image data sets in which anatomic landmarks have been (e.g., manually) annotated. The annotated landmarks may then be used to calculate a reward function or, vice versa, a loss function as a measure for the goodness of a behavior (a parameter configuration) and to punish "bad" actions of the trained function and reward "good" actions of the trained function.

The first and second trained functions being different may mean, in other words, that first and second trained functions are independent from one another in the sense that they do not share layers, parameters, weights or functional elements. By consequence, first and second trained functions would be fully functioning as stand-alone implementations. According to an embodiment, being different may mean that first and second trained functions have been trained independently.

First and second trained functions may be seen as being comprised in an intelligent agent which outputs the second set of landmarks to a user or to ensuing additional processing steps such as an automated follow-up analysis, image segmentation or similar case search. As yet a further possibility, the output of the second trained function (i.e., the second set of landmarks) may be used by another trained function as a starting point for an additional refinement step of the landmark detection at an even higher resolution.

The proposed solution of at least one embodiment thus is a multi-resolution or multi-scale approach to the landmark detection problem. It breaks the problem down into at least two independent searches for anatomic landmarks, one search taking place at a comparably coarser resolution of the received medical image data and one taking place at a finer resolution. Thereby, the search at the finer second resolution makes use of the results found at the coarser resolution. Using the first set of landmarks by the second trained function may mean that the anatomic landmarks comprised in the first set of landmarks are used for determining the second set of landmarks. Specifically, the landmark locations output by the first trained function may be used as starting points for the second trained function.

The method steps as introduced above synergistically contribute to a method facilitating an efficient and robust landmark detection. In particular, using at least two different searches at different resolutions allows to quickly narrow down the analysis to the most relevant parts of the medical image data. In a first coarse search, potentially relevant regions may be identified which may then be further analyzed in the subsequent refinement step at the higher resolution. By leveraging information from the lower resolution, image processing at the higher resolution only requires roughly the same computational complexity as at the lower resolution, even when detecting a larger number of landmarks at the higher resolution. That is, the analysis at the higher resolution may focus on the most relevant spots of the medical image data which decreases computation times and memory usage. The use of distinct trained functions for each resolution thereby allows to specifically train the algorithms for the detection task which improves the accuracy and the convergent behavior of the method. In turn, also the computational costs during training and the amount of training data needed may be advantageously reduced. The improvements achieved by the proposed method therefore cover the entire value chain from training to deployment and thus optimally assist a user in providing a medical diagnosis by processing medical image data.

Thus, in other words, a computer implemented method for detecting one or more anatomic landmarks in medical image data is provided, comprising the steps of: receiving medical image data depicting a body part of a patient, generating at least a first and a second representation from the medical data, the first representation having a lower image resolution than the second representation, detecting one or more anatomic landmarks in the first representation by applying a first trained function to the first representation, the first trained function being trained to iteratively improve a predicted landmark location at the first resolution, for each of the one or more anatomic landmarks, inputting the predicted landmark location into a second trained function, and improving the predicted landmark location output by the first trained function by applying a second trained function to the second representation, the second trained function being trained to iteratively improve the predicted landmark location at the second resolution.

According to an embodiment, the trained functions are machine learned (artificial) neural networks, convolutional neural networks and/or a (convolutional) policy networks. A neural network is basically built up like a biological neural net, e.g., a human brain. In particular, an artificial neural network comprises an input layer and an output layer. It may further comprise a plurality of layers between input and output layer. Each layer comprises at least one, preferably a plurality of nodes. Each node may be understood as a biological processing unit, e.g., a neuron. In other words, each neuron corresponds to an operation applied to input data. Nodes of one layer may be interconnected by edges or connections to nodes of other layers, in particular, by directed edges or connections. These edges or connections define the data flow between the nodes of the network. In particular, the edges or connections are equipped with a parameter, wherein the parameter is often denoted as "weight". This parameter can regulate the importance of the output of a first node to the input of a second node, wherein the first node and the second node are connected by an edge.

According to an embodiment, first and second trained functions are deep reinforcement machine-learnt networks.

By relying on reinforcement learning, it is possible to provide trained functions capable of decomposing a complex problem into a plurality of individual steps. At each step, the trained function may evaluate its current state on the basis of the input data and decide about the next action to advance to the next state. Applied to the present landmark detection problem, a current state may be seen as the current estimate for the landmark location and the state may be sampled using the image data, at least in a region around the current landmark location. The actions may involve moving the current landmark location in the respective image representation to advance to a new (improved) landmark location. This process may iteratively continue until the actions lead out of the image space (indicating that there are no valid landmarks comprised in the image data) or convergence is reached (i.e., there are no actions left to further improve the detected landmark location). Because of that, search strategies implemented by reinforcement learnt trained functions optimally complement the multi-scale approach introduced above. Subdividing a problem into multiple partial problems in machine learning has the benefit that convergence behavior is improved, meaning that the trained functions are faster and yield better results. Moreover, the trained functions become more flexible in the sense that they may be applied to a considerably greater variety of medical image data. Thus, the usage of reinforcement learnt trained functions synergistically contributes to a method improved in terms of speed, accuracy and flexibility.

According to an embodiment, first and second trained functions respectively are implemented as policy networks.

A policy network may be seen as a trained function following a certain learned policy for iteratively performing a plurality of actions in order to fulfill the learned task. The policy of the trained functions may be defined as the ability to select a next action to position the state on the landmark target of the medical image data such that the long-term reward is favored. In other words, the way how distinct actions are selected starting at a given state of the trained functions is called "policy". The trained functions thus include a policy for actions on how to detect anatomic landmarks. Thereby, iterative repositioning steps may evolve the current estimate for the landmark location according to the policy, eventually identifying landmark locations in the respective representation and at the corresponding resolutions. Implementing the trained functions as policy networks thus may be seen as one embodiment of reinforcement learnt trained functions. Using policy networks brings about the above-explained advantages of more versatile, faster and reliable algorithms.

One consequence of breaking the landmark detection problem down into multiple iteratively performed steps is that traditional learning schemes such as supervised learning become inadequate. This is because there usually only exist labels for the final state, i.e., the actual landmark location, and not for the intermediate states on the way towards the final state. Thus, the first and second trained functions have to learn to take actions in an environment in order to maximize some notion of a future cumulative reward (which will materialize when the actual landmark locations are reached). In this respect, reinforcement learning is a technique facilitating learning as an end-to-end cognitive process for a trained function, instead of a predefined methodology. In other words, the trained functions acquire the ability to develop strategies to cope with an uncertain environment (here: the medical image data) thereby increasing their flexibility.

According to one embodiment, one reinforcement learning setting is thus composed by first and second trained functions that can interact with an uncertain environment in the form of the medical image data with the target of reaching pre-determined goals (i.e., identifying the landmark target in the image data). The trained functions may observe the state of the environment (i.e., the image data in the respective representations) and choose to act on the state, similar to a trial-and-error search, maximizing the future reward signal received as a response from the environment. The reward value can indicate, for instance, a distance metric between the current state and a landmark target of the medical image.

According to an embodiment, first and second trained functions have been trained as a Markov decision process using policy gradients.

Employing a Markov decision process effectively means that the individual states and actions are regarded as being statistically independent of the preceding states. This is the basis of an approach of iteratively determining optimal policies during training. For each state, an action would be good that maximizes the future (cumulative) reward (cumulative because the individual rewards for each future action are summed up until convergence is reached). In Q Learning, a function representing the future reward for each state and action is learned directly, e.g., by using deep neural networks as approximators (Deep Q Learning). First and second trained functions thus would become capable of directly outputting a discrete quality value for each of the possible actions in a state and thus choose the action with the best future cumulative reward value.

The inventors of this application have recognized that the direct learning of an approximation for the future reward may become exceedingly complex since this approximation would have to map all the different states and actions possible in the landmark detection problem. As an alternative, the inventors suggest directly optimizing the policy space rather than deriving the optimal policy from an approximation for the maximal future reward. Mathematically, optimizing the policy space can be formulated as an optimization problem based on gradients of the policy (policy gradients). Using policy gradients is beneficial if the training data is scare and/or the input to the trained function is variable. Thus, employing a Markov decision process using policy gradients complements the multi-resolution detection scheme introduced above as it renders the individual detection steps more reliable at all scales which multiplies the overall accuracy of the method.

According to an embodiment, first and second trained functions may thus be seen as being respectively trained to maximize a cumulative future reward value for a sequence of actions for identifying the first and second sets of landmarks, preferably by respectively evaluating the gradient of the respective cumulative future reward with respect to one or more parameters of the respective trained function.

According to an embodiment, first and second trained functions are respectively trained to define one or more subspaces in first and second representations, respectively. Further, they are trained to specify sequences of actions based on a learned policy to reposition the one or more subspaces in first and second representations so as to respectively parse first and second representations for determining first and second sets of landmarks in one or more iterations of repositioning the sub-spaces.

In other words, first and second trained functions are respectively configured to iteratively improve a predicted landmark location by defining a sub-space around the predicted landmark location in the respective representation and reposition the sub-space in the respective representation in one or more iterations following a learned policy.

The landmark detection problem is thus subdivided into partial problems of determining if and how a sub-space is to be repositioned so as to be moved towards a landmark location. By constricting the analysis to sub-spaces, it is not necessary to sample the entire image data comprised in the representation at once. Rather, the evaluation may be constricted to a clearly defined region of interest in the form of the sub-space. This reduces the complexity of the trained functions thereby facilitating training and reducing computation times. What is more, by subdividing the image data into sub-spaces, the method becomes more versatile since sub-spaces may have a higher degree of similarity amongst different studies as compared to the full field of view (which may be offset, partially blurred, etc.). Defining subspaces in the respective representation to be analyzed is combined with applying an intelligent strategy of repositioning the sub-spaces in the image space. Starting from a given sub-space, an optimal strategy for positioning the sub-space in the next step is determined which gives the highest likelihood for advancing towards the actual landmark location. Accordingly, the trained functions do not need to sample the entire image space but only a fraction of it (according to the trajectory pursued for repositioning) thereby further decreasing the computational costs. In a way, the trained functions thus focus on finding a balance between exploration (of uncharted territory) and exploitation (of current knowledge).

The behavior of the first and second trained functions may be seen as the intelligent selection of next actions that advance a position of the sub-space on a target landmark in the respective the representation of medical image data in such a way that the cumulative future reward is maximized. That is, first and second trained functions learn to determine the most favorable sequence of position changes required to accurately detect an anatomic landmark. Thus, a state of the trained functions may be modeled as a current candidate position for the landmark target and a fixed region (in the form of the sub-space) around the candidate position. For example, a state for a three-dimensional representation may be a cubic region with a defined width, length and depth in voxels. The candidate position for the state may be the coordinate point in the center of the cube. First and second trained functions selectively evaluate image data defined by the current state. The subsequent behavior for the candidate position is responsive to what is observed within the state. A state is composed of parameters that are used to establish a focal point (e.g., one particular coordinate, pixel, or voxel), while also permitting limited perception of the surrounding context.

According to an embodiment, the actions for repositioning comprise moving the sub-space in the respective representation to the left, to the right, up, down, forwards or backwards and, optionally, combinations thereof. Further, the actions for repositioning may comprise scaling and/or rotating the sub-spaces.

According to an embodiment, first and second trained functions are respectively trained to output, in each iteration, a probability distribution corresponding to actions for repositioning the one or more sub-spaces in the first and second representations respectively, and to reposition the one or more sub-spaces by sampling the probability distribution.

Determining the next actions based on a probability distribution (rather than by calculating concrete reward values for each action) has the advantage, that the method becomes more readily applicable to continuous, finely discretized actions or generally large action spaces. In the case of the landmark detection problem, the inventors already observed an increased performance even if only elementary actions of moving the sub-space are allowed (in three dimensions these are moving the sub-spaces up, down, back, forth, left or right). Furthermore, probability distributions readily enable combining two or more of these actions in one iteration. Moreover, probability distributions offer the possibility to introduce even more complex actions such as repositioning by a variable number of pixels/voxels, rotating the sub-spaces and/or scaling the sub-spaces in order to implement even more elaborate and more effective policies for parsing first and second representations.

According to an embodiment, the probability distributions reflect a learned policy of first and second trained functions, which policy has been learned by evaluating a gradient of a respective cumulative future reward with respect to one or more parameters of the respective trained function.

According to an embodiment, first and second trained functions are configured to improve the predicted landmark location until either a point of convergence of a likely landmark location is found or the trajectory of improved predicted landmark locations leaves the image space of the respective representation without reaching a point of convergence.

Effectively, this means that the intelligent agent is also capable of handling searches that do not lead to a landmark location. Instead of outputting a wrong or inadequate landmark location it may thus also terminate the search without having reached a landmark location.

According to an embodiment, improvement of the predicted landmark location by the second trained function starts with the corresponding point of convergence of a likely landmark location as determined by the first trained function.

This means that the information gathered by the first trained function may be tickled down to the next resolution level in order to avoid redundant search steps.

According to an embodiment, the second trained function is configured to define one or more of the subspaces based on landmark locations of the first set of landmarks.

In other words, this means that the landmark locations detected by the first trained function are used as starting points for the detection at the higher resolution. This has the benefit that the second trained function typically requires less iterations before converging to a landmark location in the second resolution. This is particularly important as the search at the higher resolution otherwise would require considerably more computational time due to the increased amount of information.

According to an embodiment, the first trained function is configured to define one or more of the sub-spaces based on a set of starting values. Thereby, the set of starting values preferably comprise average locations from known locations of anatomic landmarks extracted from a plurality of comparative medical image data sets depicting the body part.

For instance, these average locations may be taken by averaging landmark locations from the training data sets. In doing so, the starting values constitute a good first estimate for predicted landmark locations. As such, the number of iterations required by the first trained function may be reduced resulting in faster computation times.

In other words, improvement of the predicted landmark location by the first trained function starts with a corresponding starting value, the starting value being either a stochastic starting value or being generated by averaging verified locations of landmarks from prior medical image data depicting the same body part.

According to an embodiment, the method further comprises the following steps: rendering an assistance image of the medical image data and displaying the assistance image with landmark locations from the second set of landmarks highlighted.

By providing the user with a rendering with the anatomic landmarks highlighted, the user can immediately infer which landmarks have been detected and where they lie. This helps guiding the image reading and therefore increases the usability of the method and provides an improved assistance to the user for deriving a medical diagnosis.

The assistance image may relate to a two-dimensional rendering. It may, in general, rely on known rendering procedures, such as ray-casting, ray-tracing, texture-rendering or the like. The term "highlighted" in this context may mean that the identified anatomic landmarks may be highlighted using symbols. Further, the identified anatomic landmarks may be highlighted using labels comprising semantic expressions. The highlighting or labeling may be carried out based on information from the intelligent agent as to the identified anatomic landmarks, such as position and/or type.

According to an embodiment, the method further comprises generating the first representation from the medical image data by sampling the medical image data at the first resolution lower than the intrinsic resolution of the medical image data, wherein, preferably, the first resolution is preset, selected by a user from a set of one or more predetermined resolutions or selected by a third trained function from a set of one or more predetermined resolutions.

The intrinsic resolution is the original or initial resolution of the medical image data. It may be determined by the imaging modality and/or the imaging parameters used or depend on one or more image preprocessing steps. Generating a (first) representation therefrom having a lower resolution therefore means down-sampling the medical image data. To this end, various known methods may be employed such as nearest neighbor interpolation, bilinear and bicubic algorithms, box sampling, fourier-transform methods and so forth. Presetting the resolution of the first representation has the advantage that it can be safely assumed that a corresponding trained function (here: the first trained function) is actually available. For the same reason, defining a number of predetermined resolutions is beneficial. In turn, this may mean that the intelligent agent comprises a trained function for each of the predetermined resolutions. First and second trained functions may be selected therefrom based on the selected resolutions. The first resolution may be selected either by the user or automatically. With regard to the latter, a further (i.e., a third) trained function may be used. The further trained function is trained to choose the first resolution which is best suited for the medical image data to be analyzed. That is, the third trained function would be trained to take in the medical image data and output the first resolution. The further trained function may be part of the intelligent agent.

According to an embodiment, the method further comprises generating the second representation from the medical image data by sampling the medical image data at the second resolution, the second resolution being either lower than or equal to the intrinsic resolution of the medical image data. Thereby the second resolution is preset, selected by a user from a set of one or more predetermined resolutions, and/or selected by a fourth trained function from a set of one or more predetermined resolutions. Thereby the fourth trained function may be part of the third trained function.

According to a further embodiment, a method for building (assembling) an intelligent agent to determine anatomic landmarks in medical image data is provided. The method comprises several steps. A first step is directed to receiving a plurality of training medical image data sets respectively depicting the body part and comprising target landmark locations. A further step is directed to receiving first and second trained functions. A further step is directed to respectively generate at least first and second representations from the training medical image data sets, the first representations having a lower image resolution than the second representations. A further step comprises training the first trained function to identify anatomical landmarks at the first resolution by employing a scheme of iterative improvement of a predicted landmark location by defining a sub-space around the predicted landmark location in the first representation and reposition the sub-space in the first representation in one or more iterations following a learned policy by applying the first trained function to the first representations and using the target landmark locations to maximize a cumulative future reward value for a sequence of actions for repositioning the sub-space in the first representations. A further step comprises training the second trained function to identify anatomical landmarks at the second resolution by employing a scheme of iterative improvement of a predicted landmark location by defining a sub-space around the predicted landmark location in the second representation and reposition the sub-space in the second representation in one or more iterations following a learned policy by applying the second trained function to the second representations and using the target landmark locations to maximize a cumulative future reward value for a sequence of actions for repositioning the sub-space in the second representations. Yet a further step is directed to assembling the first trained function and the second trained function such that the second trained function inputs the output landmark locations of the first trained function as starting values.

According to an embodiment, maximizing a cumulative future reward in training first and second trained functions comprises evaluating the gradient of the respective cumulative future reward with respect to one or more parameters of the respective trained function. Further, first and second trained functions are configured, through training, to output, in each iteration, probability distributions for actions to reposition the sub-spaces in the respective representations.

According to another embodiment, the invention further relates to a training system for building (assembling) an intelligent agent. The system comprises an interface, embodied for receiving first and second trained functions, and further embodied for receiving the training medical image data sets. The training system further comprises a processor configured to carry out the method steps according to the above method for building (assembling) an intelligent agent.

The training system's processor may in particular involve a computer, a microcontroller or an integrated circuit. As an alternative, the training system may involve a real or virtual network of computers (a real network is referred to as a cluster, a virtual network is referred to as a cloud). The interface may involve a hardware or software interface (for example PCI-Bus, USB or Firewire).

According to an embodiment, a system for detecting one or more anatomic landmarks in medical image data is provided. The system comprises an interface unit for receiving a medical image data set depicting a body part of a patient, a memory storing a first trained function trained to identify a set of anatomic landmarks in a representation of the medical image data set at a first resolution, and a second trained function trained to identify a set of landmarks in a representation of the medical image data set at a second resolution higher than the first resolution. The system further comprises a computing unit configured to apply the first trained function to a first representation of the medical image data at the first resolution so as to identify a first set of anatomic landmarks, to input the first set of anatomic landmarks to the second trained function and to apply the second trained function to a second representation of the medical image data at the second resolution so as to identify a second set of anatomic landmarks using the first set of landmarks.

According to an embodiment, the system is adapted to implement the inventive method according to one or more of the aspects and embodiments as herein described before.

The computing unit may be realized as a data processing system or as a part of a data processing system. Such a data processing system can, for example, comprise a cloud-computing system, a computer network, a computer, a tablet computer, a smartphone and/or the like. The computing unit can comprise hardware and/or software. The hardware can comprise, for example, one or more processor, one or more memories and combinations thereof. The one or more memories may store instructions for carrying out the method steps according to the invention. The hardware can be configurable by the software and/or be operable by the software. Generally, all units, sub-units or modules may at least temporarily be in data exchange with each other, e.g., via a network connection or respective interfaces. Consequently, individual units may be located apart from each other.

The interface unit may comprise an interface for data exchange with a local server or a central web server via internet connection for receiving the medical image data. The interface unit may be further adapted to interface with one or more users of the system, e.g., by displaying the result of the processing by the computing unit to the user (e.g., in a graphical user interface) or by allowing the user to adjust parameters for image processing or visualization and/or to select the medical image data.

According to another embodiment, the invention further relates to an image analysis system comprising the system for detecting anatomic landmarks in medical image data and a medical image system configured to acquire, store and/or forward follow-up medical images (comprising the reference image data and the follow-up image data). Thereby, the interface unit may be configured to receive the medical image data from the medical image system.

According to an embodiment, the medical image system comprises one or more archive stations for storing medical image data sets, which may be realized as a cloud storage or as a local or spread storage, e.g., as a PACS (Picture Archiving and Communication System). Further, the medical image system may comprise one or more medical imaging modalities, such as a computed tomography system, a magnetic resonance system, an angiography (or C-arm X-ray) system, a positron-emission tomography system, a mammography system, system for acquiring digital pathology images or the like.

According to another embodiment, the present invention is directed to a computer program product comprising program elements which induce a computing unit of a system for detecting anatomic landmarks in medical image data to perform the steps according to an embodiment of the above method, when the program elements are loaded into a memory of the computing unit.

According to another embodiment, the present invention is directed to a computer-readable medium on which program elements are stored that are readable and executable by a computing unit of a system for detecting anatomic landmarks in medical image data, in order to perform steps of an embodiment of the inventive method, when the program elements are executed by the computing unit.

The realization of an embodiment of the invention by a computer program product and/or a computer-readable medium has the advantage that already existing providing systems can be easily adopted by software updates in order to work as proposed by an embodiment of the invention.

The computer program product can be, for example, a computer program or comprise another element next to the computer program as such. This other element can be hardware, e.g., a memory device, on which the computer program is stored, a hardware key for using the computer program and the like, and/or software, e.g., a documentation or a software key for using the computer program. The computer program product may further comprise development material, a runtime system and/or databases or libraries. The computer program product may be distributed among several computer instances.

In summary, this disclosure suggests combining a deep reinforcement learning workflow with a multi-resolution scheme for use in detecting anatomic landmarks. The resulting intelligent agent may comprise deep learning networks for each resolution for providing actions (next coordinate to go) from the current coordinate. The deep learning networks may be configured to only take in a small image patch (e.g., 25*25*25 voxels) centered around the current location coordinate as input instead of the whole image, which may significantly reduce the memory usage and increase the runtime efficiency. The intelligent agent will finally output a signal coordinate of the desired landmark location. Instead of using traditional machine learning or popular end-to-end deep learning networks, the proposed deep reinforcement learning workflow can accomplish more accurate (or at least comparable) results at a much faster speed. Specifically, this method may combine the REINFORCE algorithm with the popular deep learning networks.

FIG. 1 depicts a system 1 for detecting one or more anatomic landmarks in medical image data MID according to an embodiment of the present invention. System 1 is adapted to perform the method according to one or more embodiments, e.g., as further described with reference to FIGS. 3 to 4.

System 1 comprises a user interface 10 (as part of the interface unit) and a processing system 20 (as part of the computing unit). Further system 1 may comprise a medical image system 40 for acquiring, storing and/or forwarding medical image data or medical image data sets MID. Such medical image data sets MID may be loaded from the medical image system 40, e.g., by the processing system 20 or by the user interface 10 directly.

Medical image data sets MID are three-dimensional medical image data sets acquired, for instance, using a computed tomography system or a magnetic resonance imaging system. The image information is encoded in a three-dimensional array of k times m times n voxels. Further, medical image data sets MDI may relate to two-dimensional medical images, for instance acquired with an X-Ray facility, with the image information being encoded in m times n pixels. In general, any imaging modalities and scanners may be used, such as ultrasound, x-ray, angiography, fluoroscopy, positron emission tomography, single photon emission computed tomography, or others. Generally, medical image data set MID shows a body part of a patient. The body part depicted in medical image data set MID will comprise various anatomies and organs. Considering the chest area as body part, medical image data set might, for instance, depict the lung lobes, the rib cage, the heart, lymph nodes, and so forth. Medical image data MID may be formatted according to the DICOM format. DICOM (=Digital Imaging and Communications in Medicine) is an open standard for the communication and management of medical imaging information and related data in healthcare informatics. DICOM may be used for storing and transmitting medical images and associated information enabling the integration of medical imaging devices such as scanners, servers, workstations, printers, network hardware, and picture archiving and communication systems (PACS). It is widely adopted by clinical syndicates, hospitals, as well as for smaller applications like doctors' offices or practices. A DICOM data object consists of a number of attributes, including items such as patient's name, ID, etc., and also special attributes containing the image pixel data and metadata extracted from the image data.

The medical image data MID generally has an intrinsic resolution determined by the imaging modality and imaging procedure used. Subsequently, the intrinsic resolution may also be denoted as the maximal or initial resolution. Starting from the intrinsic resolution, further resolutions may be calculated by down-sampling the medical image data MID to lower resolutions or up-sampling the medical image data to higher resolutions. For each resolution, a representation MID1, MID2 of the medical image data MID may be generated. These representations MID1, MID2 may, for instance, have isotropic resolutions of 16 mm, 8 mm, 4 mm and 2 mm from coarse to fine. According to some embodiments of the present invention, only representations MID1, MID2 down-sampled from the intrinsic resolution are considered.

The body parts depicted in the medical image data may comprise (or define) one or more anatomic landmarks as biometric information universal to body parts and/or anatomies. Anatomic landmarks define the location of anatomies in the body part as depicted in the medical image data (and its representations). Anatomic landmarks may relate to biological meaningful points, regions, contours, lines, and so forth. In other words, the biometric data relates to distinctive, measurable geometric identifiers definable in the depicted body part. Specifically, anatomic landmarks may be vertices, anchor points, control points, sites, profile points, 'sampling' points, nodes, markers, fiducial markers, points in a shape that are located according to some mathematical or geometrical property, fixed points, markers, features or structures that can be defined in the body part depicted in the (reference) image data sets. Although the locations of the anatomic landmarks are given in the coordinates of the underlying medical image data MID (or its representation), the existence of the corresponding features is invariant between image data sets and just depends on the underlying body part. Specifically, the anatomic landmarks may, for instance, be selected from the group comprising: Aortic Arch Center, Aortic Root, Brachiocephalic Artery Bifurcation, Left Subclavian and Vertebralis, Right Subclavian and Vertebralis Branch, Left Subclavian Artery, Celiac Trunk, Left Common Carotid Artery, Carina Bifurcation, Heart, Left Kidney Top, Right Kidney Top, Left Lung Top, Right Lung Top, Liver Center, Liver Top, Pancreas, Renal Bifurcation, Sternum Tip, Vertebral Bodies: C7, T1, T2, ..., T11, T12, L1.

User interface 10 comprises a display unit 11 and an input unit 12. User interface 10 may be embodied by a mobile device such as a smartphone or tablet computer. Further, user interface 10 may be embodied as a workstation in the form of a desktop PC or laptop. Input unit 12 may be integrated in display unit 11, e.g., in the form of a touch screen. As an alternative or in addition to that, input unit 12 may comprise a keyboard, a mouse or a digital pen and any combination thereof. Display unit 11 is configured for displaying representations of the medical image data set MID and/or the result of the landmark detection as performed by processing system 20.

User interface 10 further comprises an interface computing unit 13 configured to execute at least one software component for serving display unit 11 and input unit 12 in order to provide a graphical user interface for allowing the user to select the medical image data MID to be further analyzed and instruct the processing unit 20 accordingly, e.g., within the graphical user interface. In addition, interface computing unit 13 may be configured to communicate with medical image system 40 or processing system 20 for receiving the medical image data MID and/or the result of the image processing to be displayed to the user. The user may activate the software component via user interface 10 and may acquire the software component, e.g., by downloading it from an internet application store. According to an example, the software component may also be a client-server computer program in the form of a web application running in a web browser. The interface computing unit 13 may be a general processor, central processing unit, control processor, graphics processing unit, digital signal processor, three-dimensional rendering processor, image processor, application specific integrated circuit, field programmable gate array, digital circuit, analog circuit, combinations thereof, or other now known device for processing image data.

Processing system 20 may comprise sub-units 21-23 configured to process medical image data MID for detecting one or more anatomic landmarks. Processing system 20 may be an image processor. The image processor may be a general processor, central processing unit, control processor, graphics processing unit, digital signal processor, three-dimensional rendering processor, image processor, application specific integrated circuit, field programmable gate array, digital circuit, analog circuit, combinations thereof, or other now known device for processing image data. The image processor is a single device or multiple devices operating in serial, parallel, or separately. The image processor may be a main processor of a computer, such as a laptop or desktop computer, or may be a processor for handling some tasks in a larger system, such as in the imaging system or the server. The image processor is configured by instructions, design, hardware, and/or software to perform the steps discussed herein. Alternatively, processing system 20 may comprise a real or virtual group of computers like a so called 'cluster' or 'cloud'. Such server system may be a central server, e.g., a cloud server, or a local server, e.g., located on a hospital or radiology site. Further, processing system 20 may comprise a memory such as a RAM for temporally loading the medical image data MID or representations MID1, MID2 derived therefrom for further processing. Alternatively, such memory may as well be comprised in user interface 10.

Sub-unit 21 is an image representation generation module or unit. It is configured to generate one or more representations MID1, MID2 of the medical image data set MID by sampling the medical image data set MID at one or more predetermined resolutions. The resolutions may be set automatically by system 1 or manually by the user. Concerning the latter, the interface computing unit 13 may be configured to execute at least one software component for serving display unit 11 and input unit 12 in order to provide a graphical user interface allowing the user to select at least two different resolutions from the available resolutions for the ensuing landmark detection. Further, system 1 may be configured to make suggestions for appropriate resolutions to the user which he may accept via the graphical user interface. For generating the representations MID1, MID2 of the medical image data at the desired resolutions, sub-unit 21 is configured to run up- or down-scaling algorithms for changing the resolution of image data generally known in the art.

Sub-unit 22 is an intelligent agent module or unit configured to apply an intelligent agent 100 to the image representations MID1, MID2 generated by sub-unit 21 in order to detect one or more anatomic landmarks in the medical image data. As will be explained in more detail below, intelligent agent 100 for each of the predetermined resolutions comprises a specifically trained function TF1, TF2. That is, the landmark detection performed by intelligent agent 100 running in sub-unit 22 is a multiscale process going from coarse resolutions to finer resolutions. Each refinement step takes the results (i.e., the landmark locations) gathered at the previous (coarser) resolution as starting points to come to a better estimate for the actual landmark position.

Sub-unit 23 is a visualization and results generation module configured to translate or convert the anatomic landmarks identified by sub-unit 22 into a suitable representation for displaying to the user. The suitable representation can be in the form of an assistance image AI in which the landmarks are visually encoded. This may mean that the landmark locations are highlighted and/or supplemented with a brief textual description. Sub-unit 23 may further be configured associate the detected landmarks with the medical image data MID either by encoding this information in the medical image data directly (e.g., by using a suited DICOM field) or by generating an appropriate supplementary data file which may be associated to the medical image data MID using appropriate electronic data identifiers (such as the patient ID and/or the accession number of the underlying examination). Sub-unit 23 may further be configured to archive the information gathered by sub-unit 22 in landmark locations and/or the assistance image in the archive and review station.

The designation of the distinct sub-units 21-23 is to be construed by ways of example and not as limitation. Accordingly, sub-units 21-23 may be integrated to form one single unit or can be embodied by computer code segments configured to execute the corresponding method steps running on a processor or the like of processing system 20. The same holds true with respect to interface computing unit 13. Each sub-unit 21-23 and interface computing unit 13 may be individually connected to other sub-units and or other components of the system 1 where data exchange is needed to perform the method steps. For example, sub-unit 21 may be connected to the medical image system 40 for retrieving the medical image data MID and/or to interface computing unit 13 for forwarding/showing the assistance image AI to the user via user interface 10. Processing system 20 and interface computing unit 13 together may constitute the computing unit 30. Of note, the layout of computing unit 30, i.e., the physical distribution of interface computing unit 13 and subunits 21-23 is, in principle, arbitrary. For instance, subunit 23 (or individual elements of it or specific algorithm sequences) may likewise be localized in user interface 10. The same holds true for the other sub-units 21-23. Specifically, processing system 20 may also be integrated in user interface 10. As already mentioned, processing system 20 may alternatively be embodied as a server system, e.g., a cloud server, or a local server, e.g., located on a hospital or radiology site. According to such implementation, user interface 10 could be designated as "frontend" or "client" facing the user, while processing system 20 could then be conceived as "backend" or server. Communication between user interface 10 and processing system 20 may be carried out using the https-protocol, for instance. The computational power of the system may be distributed between the server and the client (i.e., user interface 10). In a "thin client" system, the majority of the computational capabilities exists at the server. In a "thick client" system, more of the computational capabilities, and possibly data, exist on the client.

Medical image system 40 is generally configured for acquiring and/or storing and/or forwarding medical image data sets MID. For instance, medical image system 40 may comprise an archive/review station 42 for storing reference image data RI and/or follow-up image data FI. Archive/review station 42 may be realized as a cloud storage. Alternatively, archive/review station 42 may be realized as a local or spread storage, e.g., as a PACS (Picture Archiving and Communication System). Archive/review station 42 may further store further clinical information related to medical image data sets MID, wherein the clinical information may comprise, e.g., related medical findings, personal information related to the patient under consideration, patient records or the like. Alternatively, a further database (not shown) may store this related information. Further, medical image system 40 may comprise a medical imaging modality 41, such as a computed tomography system, a magnetic resonance system, an angiography (or C-arm X-ray) system, a positron-emission tomography system, a mammography system, system for acquiring digital pathology images or the like.

Individual components of system 1 may be at least temporarily connected to each other for data transfer and/or exchange. User interface 10 communicates with processing system 20 via interfaces to exchange, e.g., medical image data set MID or the result of the computation, e.g., in the form of assistance image AI. For example, processing system 20 may be activated on a request-base, wherein the request RS is sent by user interface 10. Further, processing system 20 may communicate with medical image system 40 in order to retrieve one or more medical image data sets. As an alternative or in addition to that, user interface 10 may communicate with medical image system 40 directly. Medical image system 40 and, in particular, archive/review station 42, may likewise be activated on a request-base, wherein the request is sent by processing system 20 and/or user interface 10. Interface for data exchange may be realized as hardware- or software-interface, e.g., a PCI-bus, USB or fire-wire. Data transfer may be realized using a network connection. The network may be realized as local area network (LAN), e.g., an intranet or a wide area network (WAN). Network connection is preferably wireless, e.g., as wireless LAN (WLAN or Wi-Fi). Further, the network may comprise a combination of different network examples. Specifically, the network may comprise a network compatible with the DICOM-standard (Digital Imaging and Communications in Medicine) and the retrieval of the medical imaged data set MID may be carried out by a DICOM query and retrieve application class. Likewise, archiving the assistance image AI in medical image system 40 may be carried out using the DICOM query and retrieve application class. Interfaces for data exchange together with the components for interfacing with the user may be regarded as constituting the aforementioned interface unit.

Figure 2:
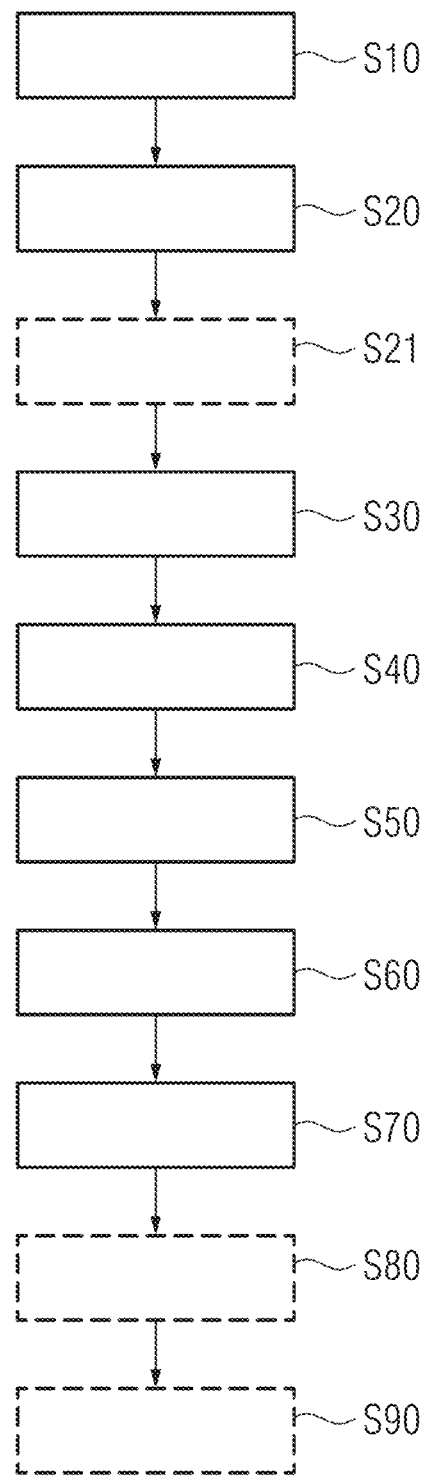
FIG. 2 depicts a flowchart illustrating a method for detecting one or more anatomic landmarks in medical image data according to an embodiment, FIG. 3 schematically shows data streams associated with a method for detecting one or more anatomic landmarks in medical image data according to an embodiment.
Figure 3:
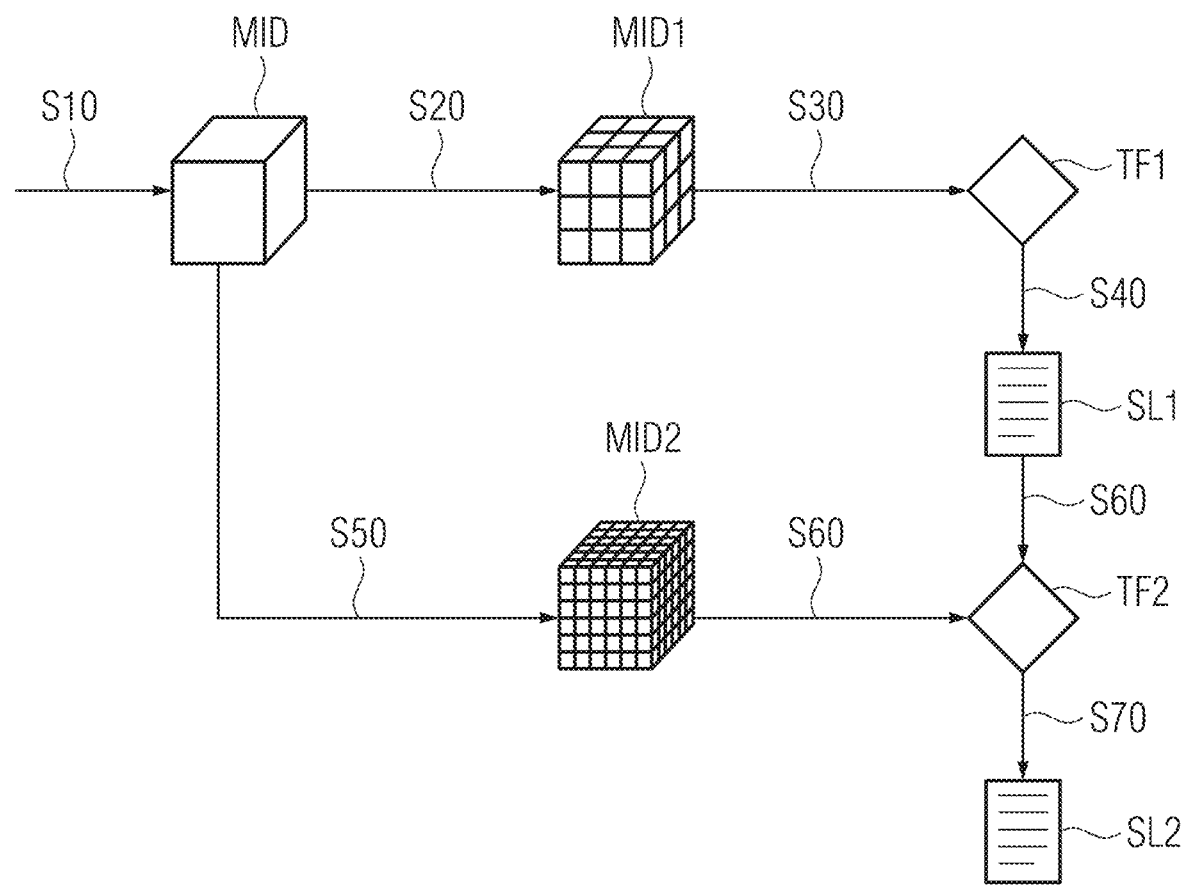

FIG. 2 depicts the inventive method for detecting anatomic landmarks in medical image data sets MID according to an embodiment of the present invention. Corresponding data streams are illustrated in FIG. 3. The method comprises several steps. The order of the steps does not necessarily correspond to the numbering of the steps but may also vary between different embodiments of the present invention. Optional steps are shown with dashed frames in FIG. 2.

In a first step S10, the medical image data MID to be analyzed is received (or provided). This may involve selecting medical image data MID, e.g., stored in the medical image system 40. The selection may be performed manually by a user, e.g., by selecting appropriate image data sets MID in a graphical user interface running in the user interface 10. Moreover, the selection may be carried out automatically, e.g., on a request base as a preprocessing step for further image processing operations, or semi-automatically by the system. In particular, this may involve automatically querying appropriate databases 42 for medical image data MID for an examination currently under review by the user. Step S10 may be performed at least partially either on user interface 10 or on processing system 20. Corresponding data exchange is included in this step where necessary.

At subsequent step S20, a first representation MID1 is generated based on the medical image data MID. The first representation has a first resolution. The first resolution is a comparably low resolution. It allows for a comparably rapid first search for regions of interests which may then be analyzed further at higher resolutions. Accordingly, the first representation usually comprises a down-sampled version of the medical image data MID. For instance, while the overall isotropic resolution of the medical image data MID is 2 mm, the first representation MID1 may have a resolution of 16 mm, 8 mm or 4 mm.

In optional step S21, a set of starting values SV may be generated which may serve as starting positions for the intelligent agent 100 (the first trained function TF1) to begin the search for landmark locations from. As such, the starting values may comprise likely starting locations for landmark locations. According to an embodiment, these may be derived from known landmark locations for the body part under consideration, for instance, by averaging a plurality of known landmark locations for the body part. "Known" in this context may relate to landmark locations having been annotated previously by an expert or to landmark locations previously detected by the intelligent agent 100 or combinations thereof. Step S21 is optional in the sense that the first trained function may also be initialized with random starting values so that Step S21 may be dispensed with. Step S20 (including optional step S21) may be performed predominately on processing system 20.

At Step S30 the first representation MID1 is input into the corresponding first trained function TF1. The first trained function TF1 has been trained to detect landmark locations at the resolution of the first representation MID1. Alongside the first representation MID1, the first trained function TF1 may also be provided with the starting values from optional step S21. According to an embodiment, Step S30 is performed predominately on processing system 20.

In Step S40, the first trained function TF1 generates a first estimate for landmark locations by detecting possible landmarks at the first resolution. The possible landmarks at are combined to form the first set of landmarks SL1. According to an embodiment, the first trained function TF1 is configured to search the first representation by iteratively moving from the starting values (which may be random values) to the likely landmark locations. As will be further detailed below, the trajectory followed in this process may be based on a learned policy for moving a sub-space SUB1 through the image space of the respective representation until the subspace comprises one or more landmarks. The sub-spaces SUB1 may be conceived as a current focus area or region of interest of the trained function TF1. For instance, the sub-spaces SUB1 may be defined by the trained function such that they are centered around the current focus. Thus, initially, the sub-spaces SUB1 are centered around the respective starting values, while the end state comprises sub-spaces centered around the predicted landmark locations. What trained function TF1 thus outputs is a first set of landmarks SL1 comprising possible landmark locations at the first resolution. The set of landmarks SL1 may in principle comprise any number of landmarks. In particular, it may also be empty and comprise zero landmarks. According to an embodiment, Step S40 is performed predominately on processing system 20.

The first set of landmarks SL1 found by the first trained function TF1 may be used as starting points for refined landmark searches at higher resolutions. To this end, a second representation MID2 having a higher resolution than the first representation MID1 is generated in Step S50. Like the first representation MID1, the second representation may be generated by down-sampling the medical image data MID. As an alternative and depending on the medical image data and the available trained functions TF2, the initial (original) resolution may be relied upon for generating the second representation without re-sampling. According to an embodiment, Step S50 is performed predominately on processing system 20.

In Step S60, the second representation MID2 and the first set of landmarks SL1 are input into the second trained function TF2. According to an embodiment, the second trained function TF2 has the same basic layout and follows the same basic working principle as the first trained function TF1. However, the second trained function TF2 has been trained to predict landmark locations at the second resolution. According to an embodiment, Step S60 is performed predominately on processing system 20.

At Step S70, the second trained function TF2 takes the landmark locations from the first set of landmarks as starting values for a refined search in the vicinity of the (coarse) estimate as provided by the first trained function TF1. Just like the first trained function TF1, the second trained function TF2 may be trained to define a sub-space SUB2 centered around the starting values (i.e., the landmark locations found by the first trained function TF1 in this case) and navigate the sub-space SUB2 to the estimated landmark location. The trajectory pursued follows a learned policy. Output by the second trained function TF2 is a second set of landmarks SL2 which is a refined estimate for the landmark locations provided by the first trained function TF1. Noteworthy, the second trained function TF2 may find additional or different or fewer anatomic landmarks than the first trained function. For instance, it is conceivable that a prospect landmark location at the first resolution turns out to be a scaling artefact. The second set of landmarks SL2 may either be considered as a final result and used for further processing or as an intermediate result for further refinement at even higher resolutions using yet additional trained functions. According to an embodiment, Step S70 is performed predominately on processing system 20.

In optional step S80, the results as provided by the intelligent agent 100 are used to generate a visualization for the user. In general, the visualization may comprise rendering one or more representations of the medical image data set MDI with the finally detected landmarks (i.e., the second set of landmarks SL2) highlighted for the user, e.g., by introducing symbols or text and/or applying designated colors. The result of the rendering can be in the form of one or more assistance images AI indicating to the user where the landmarks are and/or what type they are. The rendering may be a two-dimensional rendering on the basis of an appropriate representation of the medical image data MID such as a cross-section or slice through the image volume. The representation may be selected manually by the user, e.g., by scrolling through the medical image data set MID, or (semi)automatically by the system. Further, known volumetric rendering techniques such as ray-tracing, ray-casting or the like may be employed. In this regard, the user may specify parameters such as the viewing angle or the viewing distance. Preferably, this can be done in an interactive manner via user interface 10 with the help of a suited graphical user interface. Step S80 may be performed at least partially either on user interface 10 or on processing system 20. Corresponding data exchange is included in this step where necessary.

In optional step S90, the result of the processing of steps S10-S80 is forwarded to the medical image system 40 for archiving the results for later use alongside with the medical image data MID. In terms of results, any output of the intelligent agent 100 and any outcome of the ensuing further processing steps may be archived, in particular, the second set of landmarks SL2 and/or the assistance image(s) AI. Preferably, step S90 is implemented such that the user has to actively decide whether or not she or he wants the evaluation results to be archived. This can be realized by a corresponding button in the graphical user interface running in user interface 10, for instance. Step S90 may be performed at least partially either on user interface 10 or on processing system 20. Corresponding data exchange is included in this step where necessary.

There are various modifications and generalizations possible concerning the method explained in connection with FIGS. 2 and 3. To begin with, the detection scheme is not limited to two scales only. Basically, any number of scaling steps can be added to the method shown in FIG. 2 in order to further refine the detection process. For each additional resolution, an additional specifically trained function will be included to intelligent agent 100. These trained functions may have the same basic layout as trained functions TF1 and TF2. Each of the additional trained functions will take the landmark locations detected by the trained function at the previous coarser resolution for use as starting values. Moreover, as yet a further modification, steps S30 and S60 of calculating the representation images MID1, MID2 may also be performed together in one step preceding the ensuing landmark detection. That is, the method may comprise a step where all the representations required for input to the trained functions are calculated at once. Of note, dependent on the number of up-scaling steps, also more than two representations may be calculated. If, for instance, three predefined resolutions are to be searched, three representations will be provided by the method and so forth. In addition, the calculation of the landmarks at the different resolutions does not need to be carried out sequentially in the sense that first the detection of the first set of landmarks SL1 is finalized before moving on to the next resolution level. Rather, the refinement of the landmark localizations may be parallelized for different candidate landmarks.

According to an embodiment, the trained functions TF1, TF2, are trained to iteratively parse medical image data MID to detect on or more landmarks in the given representation of the underlying medical image data MID. Specifically, according to an embodiment, the trained functions TF1, TF2 are deep reinforcement machine learnt functions which are trained to control a sequence of actions a for employing an optimal search strategy or policy for landmark detection. In other words, trained functions TF1, TF2 according to an embodiment underwent reinforcement learning or deep reinforcement learning (wherein deep learning uses a neural network). As will be shown in the following, reinforcement learning learns to decide next acts a in an action space given an image representation.

For diving into the reinforcement learning, supervised learning is a good starting point. In ordinary supervised learning, a representation of the medical image data MID would be fed to an intelligent agent, e.g., a neural network. The return values of the intelligent agent would be coordinates for spots in the medical image data the intelligent agent identified as likely relating to landmarks. In supervised learning, there is access to a label or ground truth in the form of known landmark locations. For example, the correct landmark locations for medical image data MID might be known from annotations done by a radiologist. In an implementation of supervised learning, this information is back-propagated to the intelligent agent for an indication how to change every one of the network's parameters to make the network slightly more likely to predict the correct landmark locations.

While this approach has proven useful for many applications, it also has some drawbacks. One of the drawbacks is that the active agent has to sample the entire medical image data set at once, which, considering a neural network, requires a fairly complex network structure with a correspondingly huge parameter space to optimally decompose the information provided. By consequence, the processing time for detecting landmarks in new image data is high. What is more, also the convergence of such an artificial agent to optimal behavioral rules takes some time an requires a fairly high amount of annotated data for training.

One idea to make up for this is investigating only a comparably small fraction of the medical image data MID at a time. The small fraction may be referred to as patch or subspace in the following. While this would clearly improve the runtime efficiency and reduce the memory usage of the algorithm, there is the issue that arbitrarily defined subspaces do not necessarily comprise the landmarks the active agent is supposed to detect in the medical image data MID. The straight-forward way to solve this would be partitioning the entire medical image data MID into subspaces and analyze the sub-spaces sequentially. While this would certainly help to decrease the internal complexity of the active agent, suchlike approach would still require sampling every single data point in the medical image data MID. More importantly, the active agent might lose the "bigger picture", i.e., superordinate structures extending beyond individual sub-spaces which may lead to one or more landmarks. Therefore, rather than fixedly partitioning the medical image data into sub-spaces, the inventors implemented a scheme where an active agent 100 is trained to freely move sub-spaces SUB1, SUB2 through the medical image data MID (or its representations MID1, MID2 at the respective resolution) until one or more sub-spaces Sub1, SUB2 containing likely landmark locations have been found. In doing so, active agent 100 would still have to process a comparably small number of image data in each iteration but gets more freedom to effectively explore the medical image data MID. Thereby, active agent 100 may, for instance, identify and follow anatomic structures which are prone to lead to landmark locations. At the same time, parts of the medical image data MID irrelevant for the task such as more or less amorphous tissue may be swept quickly or disregarded altogether. This behavior is in many ways reminiscent to animal and human visual perception systems, where condensed local information is captured around a focal point and limited global context associated from the surrounding neighborhood is acquired without factoring in all available global information.

Figure 4:
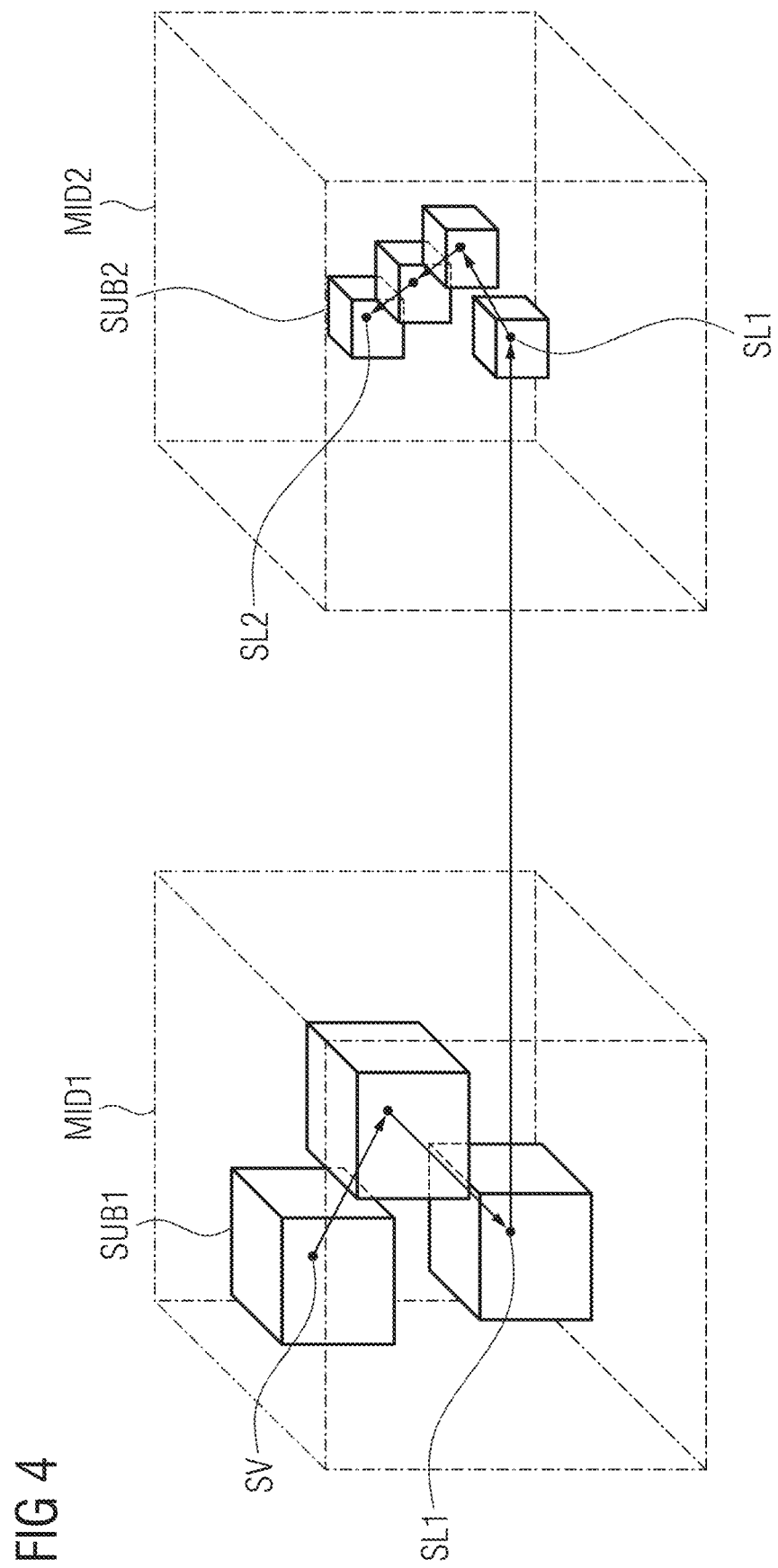
FIG. 4 illustrates a method for intelligent image parsing carried out by first and second trained functions according to an embodiment.

Putting such learned behavior of intelligent agent 100 in more mathematical terms, the sub-space SUB1, SUB2 currently under investigation may be designated as current state. In each state, the agent interacts with the enclosed environment of the medical image data MID (or the current representation MID1, MID2 of the medical image data) by selecting and performing actions a from a pre-defined set of actions. The set of actions a is chosen in such a way that agent 100 is given the possibility to explore the entire environment (c.f. FIG. 4). Located in a given state, agent 100 may choose from a set of actions a which may be defined as the discrete actions a of changing the position of the sub-space SUB1, SUB2 by one voxel or pixel in a direction specified as: front, back, upwards, downwards, left, or right with respect to the medical image data MID. Once the target has been reached (i.e., a sub-space SUB1, SUB2 comprising one or more anatomic landmarks has been found), no further action is performed, and the search is finished. Additional or alternative actions a may include rotation around an axis and/or movements by multiple voxels/pixels in each action and/or scaling actions on the sub-spaces SUB1, SUB2. Actions a may include multiple discrete steps and/or may occur simultaneously.

One issue with respect to parsing the medical image data MID by defining sub-spaces SUB1, SUB2 and iteratively repositioning them is that there is no ground truth for the iterative repositioning steps. While the landmark locations maybe annotated by a human, the optimal way (or policy) to get there for the intelligent agent 100 cannot. By consequence, supervised learning cannot be used for training artificial agent 100 to apply suitable rules or an optimal policy to choose the actions a leading to an new state. This is where reinforcement learning comes into play. Here, the annotated landmark locations serve as time-delayed labels for the performance of intelligent agent 100—the rewards. Based only on those rewards, intelligent agent 100 has to learn to derive the optimal policy for determining landmark locations. This reward-based decision process is modelled in reinforcement learning as a so-called Markov decision process (MDP). One iteration (i.e., a trajectory from a starting location to the landmark location) of this process forms a finite sequence of states, actions and rewards:

$s_0, a_0, r_1; s_1, a_1, r_2; \ldots ; s_{n-1}, a_{n-1}, r_n, s_n$.

Thereby, $s_i$ is the state, $a_i$ represents the action, and $r_{i+1}$ is the reward after performing action $a_i$. The iteration ends with the terminal state $s_n$ which is, in this case, the landmark location. According to an embodiment, the reward system may be based on the change in relative position (e.g., the focal or middle point of the sub-space SUB1, SUB2) at state $s_i$ with respect to the target location of the landmark in state $s_n$. For a move in the correct direction, a positive reward proportional to the target-distance reduction may be given, whereas a move in the wrong direction may be punished by a negative reward of equal magnitude. The reward rt at time t may thus be represented by $$r_t = \text{dist}(s_i, s_n) - \text{dist}(s_{t+1}, s_n).$$

Following the Markov assumption, the probability of the next state $s_{i+1}$ only depends on current state $s_i$ and action $a_i$ but is independent of the preceding states. However, to choose the optimal action, an artificial agent in state $s_t$ has to take into account not only the immediate reward but also the sum of the future rewards until the end state. This is usually expressed by the discounted future reward:

$$R_t = r_t + y r_{t+1} + y^2 r_{t+2} \ldots + y^{n-1} r_n.$$

Here, y is a discount factor between 0 and 1 balancing between future and immediate rewards. A good strategy for an agent would be to always choose an action a that maximizes the discounted future reward. To systematically exploit this principle, a so called quality- or Q-function is introduced which represents the maximum discounted future reward when performing action a in state s and continuing optimally from then on:

$$Q(s_t, a_t) = \max R_{t+1} = E[R_t].$$

In other words, Q may be conceived as the best possible trajectory for repositioning the sub spaces SUB1, SUB2 and finding the desired landmark location after performing action a in state s, or in other words, as expectation E. It thus represents the quality of a certain action a in state s. Despite being a theoretical construct (the actions and rewards coming after a are unknown), Q can be used to train artificial agent 100 to apply an optimal policy. One approach is to use the concept of Q learning to iteratively approximate the Q function. In practice, deep neural networks are used as the Q function approximator. This is known as Deep Q Learning (DQN). For more insights into Q-Learning and DQN, reference is made to U.S. Pat. No. 9,569,736 B1 the contents of which are incorporated herein in their entirety by reference. Having approximated the Q function, the artificial agent trained by Q learning is capable of directly outputting a discrete quality or Q value for each of the possible actions a in a state s and thus choose the action with the best Q value.

However, in connection with detecting landmarks in three-dimensional medical image data, the inventors of this application have recognized that the Q-function sometimes gets very complex. So complex, in fact, that the learning of the Q-function gets very difficult with slow convergence rates or, depending on the available training data, may fail altogether. As an alternative to Q-Learning, the inventors suggest using a learning scheme which directly optimizes the policy space rather than deriving the optimal policy from a learned Q-function. In other words, it is suggested to use active agent 100 (such as a neural network or other suitable functions) to model the probabilities p(a) of each action a. During learning, each time active agent 100 repositions the current sub-space SUB1, SUB2, the parameters of active agent 100 will be altered such that advantageous actions will be sampled more likely in the future and disadvantageous actions will be sampled less likely. This will be repeated until active agent 100 converges to an optimal policy. Formally, the objective of this approach is to maximize the future reward E[Rt] by iteratively optimizing the parameters K of the intelligent agent. This can be done by calculating the gradient of E[Rt] with respect to the parameters K. This gradient may be expressed as:

$$\nabla_K E[R_t] = E[\nabla_K \log p(a) R_t],$$

with p(a) being the likelihood for action a. If $R_t$ is large, this indicates an advantageous action a and p(a) will be increased. On the other hand, if $R_t$ is small, p(a) will be decreased. In other words, intelligent agent 100 starts with a stochastic policy that samples actions a. Actions a that happen to eventually lead to good outcomes get encouraged in the future, and actions a leading to bad outcomes get discouraged. In contrast to intelligent agents trained with Q-Learning which output Q-values, intelligent agent 100 trained according to the above policy gradient optimization scheme outputs probabilities for the actions a in the form of a probability distribution p(a). The above formulation may also be referred to as actor-critic framework, where intelligent agent 100 acts as the "actor" (i.e. sample actions) and $R_t$ acts as the "critic" to evaluate the sampled actions.

As mentioned, to further improve the performance of artificial agents 100 for the localization of anatomic landmarks, the inventors further envisioned using a multi-scale detection scheme at various resolutions derivable from the medical image data MID. Hereby, a hierarchical process from coarse resolutions to finer (higher) resolutions is implemented. For each resolution, a respectively trained function TF1, TF2 as part of intelligent agent 100 is provided. Trained functions TF1, TF2 have been specifically trained at the corresponding resolutions. In other words, for each resolution there is a corresponding trained function TF1, TF2. In general, any number of resolutions and corresponding trained functions TF1, TF2 may be used. The idea is, to search locations of an initial set of landmarks (first set of landmarks SL1) in a coarser resolution which allows for a comparably swift scan of the medical image data. The locations of the first set of landmarks SL2 may then be refined using representations of the medical image data MID at one or more higher resolutions. In this regard, the landmark locations detected at the coarser resolutions may be used as starting points for refinement at the higher resolutions. Using such multiscale detection scheme, the computational complexity of the landmark detection may be reduced since complexity is linearly related to the number of pixels or voxels considered at each resolution.

According to an embodiment, this multi-resolution approach may be combined with the intelligent image parsing following a learned policy as explained above. In this regard, FIG. 4 illustrates an example detection pipeline for detecting a landmark in medical image data MID. In this example, the search starts at a starting value SV on a first resolution level of the medical image data MID. Based on the first resolution level (which may be preset) a first representation MID1 of the medical image data set MID is generated. Active agent 100 starts at an initial state by defining a sub-space SUB1 around the starting value SV in the first representation MID1. Sub-space SUB1 represents a subset of the entire image volume at the first resolution of the medical image data set MID. For instance, sub-space SUB1 may be a rectangular volume with side lengths of 25×25×25 voxels. Starting from the initial state (i.e., sub-space SUB1 centered around the starting value SV), the first trained function TF1 parses the first representation MID1 by navigating the sub-space through the first representation MID1. Thereby, the first trained function TF1 follows a learned policy for iteratively repositioning sub-space SUB1. At each repositioning step, the first trained function TF1 determines an action a of moving sub-space SUB1 taking into account the current state (i.e., the voxel values in the current sub-space SUB1) and, optionally, the hitherto explored trajectory. Along each trajectory, a sequence of the local environment is represented by the image information in the form of the three-dimensional sub-space SUB1 centered at the current location of the first trained function TF1. When applied on 3D medical image data MID as shown in FIG. 4, the actions a consist of moving sub-space SUB1 up, down, back, forth, left, right and combinations thereof in the 3D dimensional image space—reflecting the three degrees of freedom of moving an object in a 3D space. The repositioning of sub-space SUB1 continues until an end state is reached—which may be recognized as an oscillation or infinite loop between two adjacent states of sub-spaces SUB1. The end state is considered as a high confidence result for the location of a landmark in the first representation MID1. The thus detected landmark is part of the first set of landmarks SL1.

Parsing the coarse (or coarsest) representation MID1 of the medical image data set MID with the first trained function TF1 may be conceived as a first step of the landmark detection process according to the invention. The outcome of this first step is subsequently used as a starting point for the ensuing second detection step at a second resolution higher than the first resolution (c.f., FIG. 4). The second parsing or sweep at the higher resolution is performed by the second trained function TF2, which may have the same topology and the same basic functionality as the first trained function TF1. Like the first trained function TF1, the second trained function TF2 defines a sub-space SUB2 and navigates the image by repositioning the sub-space SUB2 until convergence at an oscillation-point between neighboring voxels is reached. Since the resolution of the corresponding representation MID2 is higher, sub-spaces SUB2 typically over-sweep a smaller absolute area of the medical image data MID as compared to sub-spaces SUB1 (although sub-spaces SUB2 may have the same number of voxels as compares to sub-spaces SUB1). By consequence, the stride when parsing the second representation MID2 is finer. The process continues until a convergence point in the second representation MID2 marked as the detection result is reached, i.e., the location of the landmark in the second resolution (as part of the second set of landmarks SL2).

It should be noted that medical image data sets usually have more than one landmark. The intelligent agent 100 comprising the trained functions TF1, TF2 may be configured to detect these in parallel. In other words, intelligent agent 100 may be configured, to detect all landmarks in a first representation of the medical image data using a first trained function TF1 (i.e., all landmarks forming the first set of landmarks) before up-scaling to a second representation for determining the second set of landmarks with second trained function TF2. As an alternative, intelligent agent 100 may be configured to process each candidate landmark sequentially. Further, combinations of parallel and sequential processing may be used. While the above has been explained in connection with three-dimensional data, the process works equally well for two-dimensional data. In that case, the subspaces SUB1, SUB2 would be 2D image patches taken from 2D representations of the medical image data MID. For two dimensional problems, the actions of repositioning the sub-spaces there would only allow two degrees of freedom (e.g., up-down and left-right). Sub-spaces SUB1 and SUB2 may have the same size in voxels (or pixels), e.g., 25×25×25 voxels (or 25×25 pixels). As an alternative, sub-space SUB2 may have a bigger or smaller size in voxels (or pixels) than sub-space SUB1, e.g., a size between 80% and 120% of the size of sub-space SUB1. What is more, the size of sub-spaces SUB1 and SUB2 may be dynamically set (scaled) by the respective trained functions TF1 and TF2 according to a learned policy.

While the forgoing has been explained as a process using two resolutions for sampling the medical image data MID, it should be noted that any number of discrete scale levels going form coarse to fine can be used. For each scale level, active agent 100 comprises a trained function TF1, TF2 which has been specifically trained to predict one or more landmark locations at the respective resolution of the medical image data MID. According to an embodiment, the trained functions for the respective resolutions are independent from one another in the sense that they have been trained independently, do not share any weights or biases, and are fully functioning as stand-alone algorithms.

Figure 5:
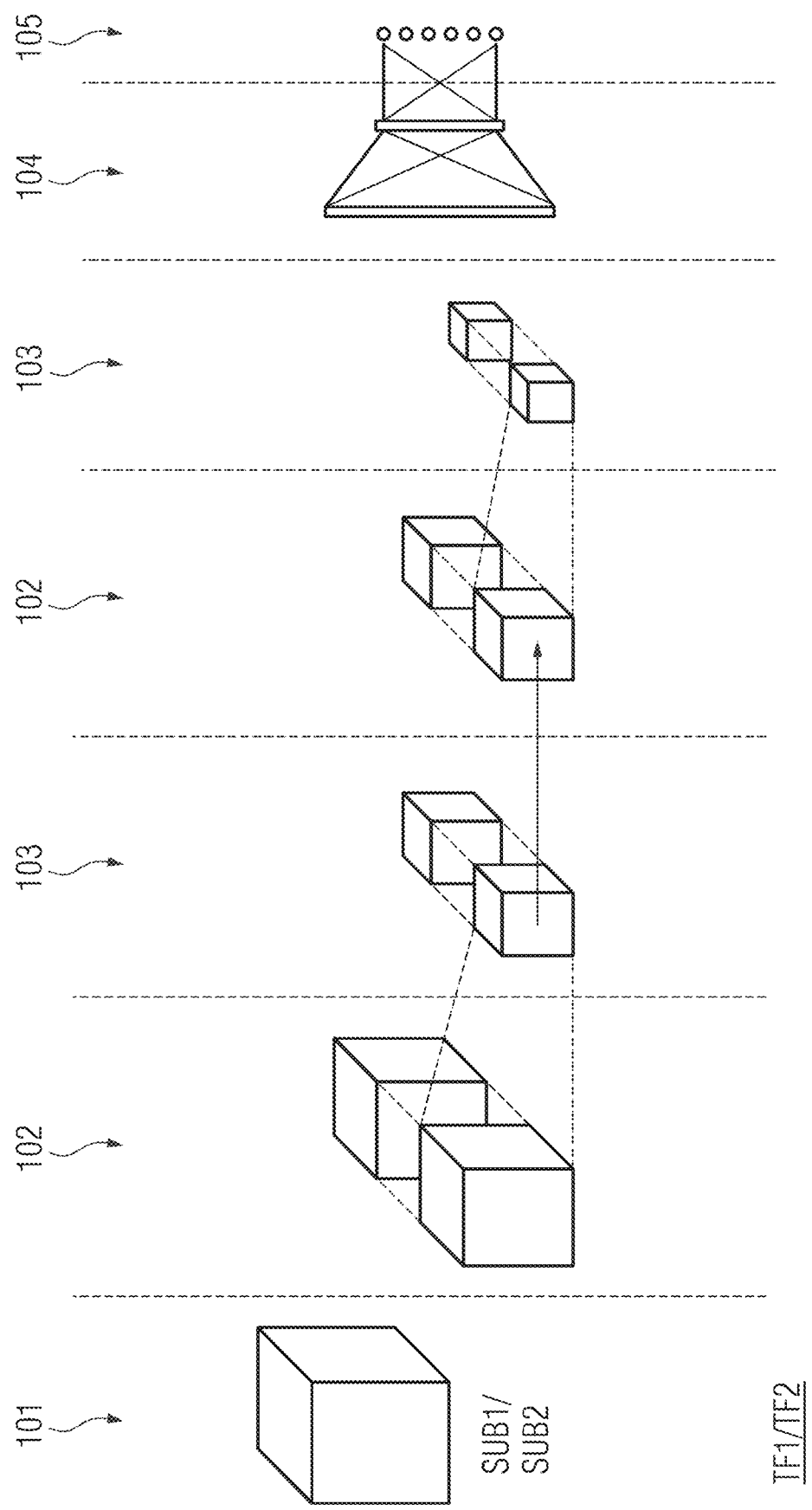
FIG. 5 depicts a general setup of first and second trained functions according to an embodiment.

FIG. 5 depicts an example representation of the structure of the trained functions TF1, TF2 which may be used in active agent 100 according to an embodiment. As can be seen from FIG. 5, the trained functions TF1, TF2 may be embodied by (deep) convolutional neural networks (CNN) inputting the sub-spaces SUB1, SUB2 centered at the current estimated landmark location. Trained functions TF1, TF2 may be policy networks configured to follow an optimal policy learned by reinforcement learning, for instance, by policy gradient optimization. As such, trained functions TF1 and TF2 may be implemented and trained to output action probabilities p(a) for parsing the underlying multi-resolution representations MID1, MID2 of the medical image data set MID with a window in the form of a sub-space SUB1, SUB2 in the corresponding representation MID1, MID2.

The trained functions TF1, TF2 are defined in the form of a plurality of sequential layers 101-107. The term sequential is used to indicate the general flow of output feature values from one layer to input to a next layer. The information from the next layer is fed to a next layer, and so on until the final output layer. Layers 101-105 may only feed forward or may be bi-directional, including some feedback to a previous layer. The layers 101-105 may be weighted. Further, each layer 101-105 generally comprises a number of nodes that are also weighted. Essentially, each node can be seen as executing a mathematical operation mapping one or more input values to an output value. The nodes of each layer may connect with all or only a sub-set of nodes of a previous and/or subsequent layer. Two nodes are "connected" if their inputs and/or outputs are connected. Further, skip connections may be used, so that layers may also output to other layers than the sequentially next layer.

In the example shown in FIG. 5, layer 101 is the input layer. Input values for the nodes of layer 101 are subspaces SUB1, SUB2 centered at the current estimate of the landmark location. Layer 107 is the output layer. Output values of the nodes of output layer 107 may be probabilities p(a) for each action a. Considering three-dimensional medical image data MID as an example, the output probabilities p(a) may correspond to the actions a of translating sub-spaces SUB1, SUB2 up, down, back, forth, left and right. Thus, output layer 105 may comprise 6 output nodes. In between input 101 and output layer 105 there is a number of hidden layers 102-104. Various layers may be used, such as convolutional 102, pooling 103 (e.g., max-pooling or average-pooling), fully connected 104, or other types of layers. Convolutional layers convolve the input and pass its result to the next layer by moving an image filter kernel over the input. Pooling layers 103 reduce the dimensions of the data by combining the outputs of node clusters at one layer into a single node in the next layer, thereby streamlining the underlying computation. A fully connected layer 104 connects every node in one layer to every node in another layer, so that essentially every feature gets a "vote". According to an example, the structure used for the trained functions TF1, TF2 may the same for all resolutions and landmark types. For instance, it may comprise the following structure: convolutional layer (32 kernels: 5×5×5), pooling (Max pooling: 2×2×2), convolutional layer (46 kernels: 3×3×3), pooling (Max: pooling 2×2×2), and three fully connected layers (512×128×6 nodes).

As can be seen in FIG. 6, two of the trained functions TF1 and TF2 may be combined to form an active agent 100 capable of iteratively sampling medical image data MID at two resolutions from coarse to fine. As already mentioned, the number of resolutions is not limited to two, however. The concept may be extended to any number of discrete resolutions, with the intelligent agent 100 then comprising a corresponding number of distinct trained functions, respectively trained for detecting landmark locations at the assigned resolution.

The trained functions TF1, TF2 of this embodiment learn by adapting weights or weighting parameters of individual layers and nodes based on training data. Rather than preprogramming potential landmark locations, the trained functions are defined to learn these locations by iteratively repositioning a region of interest based on input data. The learning may be conceived as learning a policy for navigating the sub-spaces through the medical image data at the respective resolution thereby following an optimal trajectory to the landmark location starting from a giving starting value. To do so, the trained functions TF1, TF2 may learn to recognize features in the sub-spaces SUB1, SUB2 and their relation to landmark locations. Each node of a layer may be considered representing a feature. Different layers are provided for learning different features. To give an illustrative example, one feature may be a line directly found in the sub-space SUB1, SUB2. The next layer may combine lines, so that one of the new features is a corner or intersection. The next layer may combine features (e.g., the corner and length of lines) from a previous layer so that the next layer provides a shape indication which could hint at a landmark location.

As mentioned, the trained functions TF1, TF2, according to an embodiment, are trained using a method according to reinforcement learning, in particular, using a method relying on policy gradient optimization. During training, the machine learned network 100 is applied to training input values to produce corresponding output values the target values of which are known.

FIG. 7 depicts an embodiment of an inventive method for training a trained function TF1, TF2 to determine landmark locations in representations MID1, MID2 of medical image data MID at predetermined resolutions. The method comprises several steps. The order of the steps does not necessarily correspond to the numbering of the steps but may also vary between different embodiments of the present invention. Optional steps are shown with dashed frames in FIG. 7.

A first step T10 is directed to provide a plurality of training medical image data sets T-MID-1 . . . T-MID-N. The training medical image data sets T-MID-1 . . . T-MID-N are preferably of the same type as the medical image data MID to be processed by the deployed and readily trained intelligent agent 100. Accordingly, the training medical image data sets T-MID-1 . . . T-MID-N each likewise show a body part of a patient comprising a plurality of anatomic structures and organs and have been acquired using one of the abovementioned medical imaging modalities. In particular, the training medical image data sets T-MID-1 . . . T-MID-N may be three-dimensional image volumes. However, the present invention is not limited thereto and the subsequent method steps are equally well applicable for two-dimensional data. The training image data set T-MID-1 . . . T-MID-N may be received by loading a plurality of training data sets from a database 240. Each training medical image data set T-MID-1 . . . T-MID-N contains a set of annotated anatomic landmarks T-SL-1 . . . T-SL-N. Each set of annotated anatomic landmarks T-SL-1 . . . T-SL-N may include various anatomic landmarks for which ground truth locations have been annotated, e.g., by a human expert.

A subsequent step T20 is directed to preprocess the training data sets T-MID-1 . . . T-MID-N for training. This comprises generating a plurality of training representations TR1, T-R2 with different spatial resolutions from each of the training medical image data sets T-MID-1 . . . T-MID-N in preprocessing step T21. According to an embodiment, two training representations T-R1, T-R2 are respectively generated, one with a coarse first resolution and one with a higher second resolution. According to an embodiment, one training representation T-R1 may have a isotropic resolution of 4 mm while the other hast 2 mm. However, the present invention is not limited thereto as other scale levels may also be used for the representations T-R1, T-R2, such as 8 mm or 16 mm. Further, more than two representations may be generated per training medical image data set T-MID-1 . . . T-MID-N depending on the number of refinement steps the final intelligent agent 100 is supposed to conduct. For generating the training representations T-R1 . . . T-R2, essentially the same techniques may be employed as explained before in connection with FIG. 2. A further (optional) preprocessing step T22 may be directed to converting the locations of the annotated landmarks into to respective resolutions corresponding to the training representations. According to an embodiment, this may comprise down sampling the coordinates of the annotated landmark using an appropriate technique. Yet a further optional preprocessing step T23 may be directed to define a starting location corresponding to each annotated landmark and resolution. This may comprise generating stochastic starting locations. According to an alternative, average locations of landmarks of the same type may be calculated throughout the training data and used as starting locations.

At step T30, the functions TF1, TF2 to be trained are provided or received. The trained functions TF1, TF2 may be received from an archive or memory 230. For each of the desired resolutions a separate trained function TF1, TF2 is provided.

At step T40, the data preprocessed in step T20 is (provided) input into the trained functions TF1, TF2 according to the respective resolution. That is, the trained function TF1 designated for a first resolution is provided with the representations at the first resolution and the correspondingly converted annotated landmarks and starting locations SV.

In step T50, for each of the landmarks comprised in a training set of landmarks T-SL-1, . . . T-SL-2, the trained functions TF1, TF2 are trained to identify the correct landmark location respectively in their designated resolution. Specifically, each trained function TF1, TF2 learns an optimal policy to reposition a sub-space in the respective training representation from the starting location to the annotated landmark location. Thereby, the training comprises maximizing a future reward which is calculated based on the known landmark locations. According to an embodiment, the training further comprises training the trained functions TF1, TF2 to output probabilities for repositioning the sub-spaces SUB1, SUB2 by applying reinforcement learning, in particular, by optimizing a policy gradient as described before.

At step T60, the independently trained functions TF1, TF2 are combined to form intelligent agent 100. Combining the trained functions may comprise integrating a routine for handing over the landmark locations detected by the trained function TF1 applied to the coarser resolution data to the trained function TF2 applied to the next-finer resolution data. This may comprise a routine for converting coordinates defined at coarser resolution to finer resolution, e.g., by employing known routines for up-sampling.

FIG. 8 illustrates an embodiment of a system 200 for building an intelligent agent 100 and training the trained functions TF1, TF2 comprised in the intelligent agent. The system comprises a processor 210, an interface 220, a memory 230, a storage 240, and a database 250. Processor 210, interface 220, memory 230 and storage 240 may be embodied by a computer 290. Processor 210 controls the overall operation of the computer 200 by executing computer program instructions which define such operation. The computer program instructions may be stored in memory 230 or in storage 240 and loaded into memory 230 when execution of the computer program instructions is desired. Storage 240 may be a local storage as a component of the system 200, or a remote storage accessible over a network, such as a component of a server or cloud system. The method steps illustrated in FIG. 7 may be defined by the computer program instructions stored in memory 230 and/or storage 240, and controlled by processor 210 executing the computer program instructions.

Database 250 is a storage device such a cloud or local storage serving as an archive for the training medical image data sets T-MID-1 . . . T-MID-N. Database 250 may be connected to computer 290 for receipt of one or more training medical image data T-MID-1 . . . T-MID-N by the computer 290. It is also possible to implement database 250 and computer 290 as a single device. It is further possible that database 250 and computer 290 communicate wirelessly or with wired connection through a network. Interface 220 is configured to interact with database 250.

Wherever meaningful, individual embodiments or their individual aspects and features can be combined or exchanged with one another without limiting or widening the scope of the present invention. Advantages which are described with respect to one embodiment of the present invention are, wherever applicable, also advantageous to other embodiments of the present invention.

The following points are also part of the disclosure:
1. Computer-implemented method for detecting one or more anatomic landmarks in medical image data, comprising the steps of:
receiving medical image data depicting a body part of a patient;
generating (at least) a first and a second representation from the medical image data, the first representation having a lower image resolution than the second representation;
detecting one or more anatomic landmarks in the first representation by applying a first trained function to the first representation, the first trained function being trained to iteratively improve a predicted landmark location at the first resolution;
for each of the one or more anatomic landmarks, inputting the predicted landmark location determined by the first trained function into a second trained function;
improving the predicted landmark location output by the first trained function by applying the second trained function to the second representation, the second trained function being trained to iteratively improve the predicted landmark location at the second resolution.
2. Method according to 1, wherein first and second trained functions are respectively configured to iteratively improve a predicted landmark location by defining a sub-space around the predicted landmark location in the respective representation and reposition the sub-space in the respective representation in one or more iterations following a learned policy.
3. Method according to 2, wherein first and second trained functions, in each iteration, are respectively trained to
output, based on the sub-space, a probability distribution of actions for repositioning the sub-space in the respective representation;
reposition the sub-space by sampling the probability distribution.
4. Method according to 2 or 3, wherein the actions for repositioning comprise moving the sub-space in the respective representation to the left, to the right, up, down, forwards or backwards and, optionally, combinations thereof.
5. Method according to any of the preceding points, wherein first and second trained function are configured to improve the predicted landmark location until either a point of convergence of a likely landmark location is found or the trajectory of improved predicted landmark locations leaves the image space of the respective representation without reaching a point of convergence.
6. Method according to 5, wherein improvement of the predicted landmark location by the second trained function starts with the corresponding point of convergence of a likely landmark location as determined by the first trained function.
7. Method according to any of the preceding points, wherein improvement of the predicted landmark location by the first trained function starts with a corresponding starting value,
the starting value being either a stochastic starting value or being generated by averaging verified locations of landmarks from prior medical image data depicting the same body part.
8. Computer-implemented method for training an artificial agent for automated detection of anatomical landmarks in a medical image data depicting a body part of a patient, comprising the steps of:
receiving a plurality of training medical image data sets respectively depicting the body part and comprising target landmark locations;
receiving first and second trained functions;
respectively generating (at least) first and second representations from the training medical image data sets, the first representations having a lower image resolution than the second representations;
training the first trained function to identify anatomical landmarks at the first resolution by employing a scheme of iterative improvement of a predicted landmark location by: defining a sub-space around the predicted landmark location in the first representation, and reposition the sub-space in the first representation in one or more iterations following a learned policy by applying the first trained function to the first representations and using the target landmark locations to maximize a cumulative future reward value for a sequence of actions for repositioning the sub-space in the first representations;

training the second trained function to identify anatomical landmarks at the second resolution by employing a scheme of iterative improvement of a predicted landmark location by: defining a sub-space around the predicted landmark location in the second representation, and reposition the sub-space in the second representation in one or more iterations following a learned policy by applying the second trained function to the second representations and using the target landmark locations to maximize a cumulative future reward value for a sequence of actions for repositioning the sub-space in the second representations;

assembling the first trained function and the second trained function such that the second trained function inputs the output predicted landmark locations of the first trained function as starting values.

9. Method according to 8, wherein maximizing a cumulative future reward in training first and second trained functions comprises evaluating the gradient of the respective cumulative future reward with respect to one or more parameters of the respective trained function, and first and second trained functions have been configured through training to output, in each iteration, probability distributions for actions to reposition the sub-spaces in the respective representation.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A computer-implemented method for detecting one or more anatomic landmarks in medical image data, comprising:

receiving medical image data depicting a body part of a patient;

determining a first set of anatomic landmarks from a first representation of the medical image data at a first resolution by applying a first trained function to the first representation of the medical image data; and determining a second set of anatomic landmarks from a second representation of the medical image data at a second resolution by applying a second trained function to the second representation of the medical image data, the second trained function using the first set of anatomic landmarks, the second resolution being higher than the first resolution, and the second trained function being different than the first trained function, wherein the first trained function is configured to define one or more first subspaces in the first representation and specify sequences of actions based on a learned policy to reposition the one or more first sub-spaces in the first representation to parse the first representation to determine the first set of anatomic landmarks in one or more iterations of repositioning the one or more first sub-spaces, the second trained function is configured to define one or more second sub-spaces in the second representation based on landmark locations of the first set of anatomic landmarks and specify sequences of actions based on a learned policy to reposition the one or more second sub-spaces in the second representation to parse the second representation to determine the second set of anatomic landmarks in one or more iterations of repositioning the one or more second sub-spaces, an action of the sequences of actions based on the learned policy of the first trained function includes changing a position of the one or more first sub-spaces by at least one pixel, an action of the sequences of actions based on the learned policy of the second trained function includes changing a position of the one or more second sub-spaces by at least one pixel, the first resolution is selected from a set of one or more resolutions by a third trained function based on an intrinsic resolution of the medical image data, the first resolution is lower than the intrinsic resolution of the medical image data, and the first trained function corresponds to the first resolution and is selected from a set of trained functions corresponding to each resolution of the set of resolutions.

2. The computer-implemented method of claim 1, wherein the first trained function and the second trained function are respectively trained to output, in each iteration of the one or more iterations, a probability distribution corresponding to actions for repositioning the one or more first subspaces in the first representation and the one or more second sub-spaces in the second representation, respectively; and the computer-implemented method includes repositioning the one or more first sub-spaces and the one or more second sub-spaces by sampling the probability distribution, respectively.

3. The computer-implemented method of claim 1, wherein the first trained function is configured to define one or more of the first sub-spaces based on a set of starting values.

4. The computer-implemented method of claim 3, wherein the set of starting values includes average locations from known locations of anatomic landmarks extracted from a plurality of comparative medical image data sets depicting the body part.

5. The computer-implemented method of claim 1, wherein the first trained function and the second trained function are convolutional neural networks implemented as policy networks.

6. The computer-implemented method of claim 5, wherein the first trained function and the second trained function are 3D convolutional neural networks implemented as policy networks.

7. The computer-implemented method of claim 1, wherein the first trained function and the second trained function are trained to maximize a cumulative future reward value for a sequence of actions for identifying the first set of anatomic landmarks and the second set of anatomic landmarks.

8. The computer-implemented method of claim 7, wherein
the first trained function and the second trained function are trained to maximize the cumulative future reward value for the sequence of actions for identifying the respective first set of anatomic landmarks and the second set of anatomic landmarks by respectively evaluating a gradient of the respective cumulative future reward with respect to one or more parameters of the respective first trained function or the second trained function.

9. The computer-implemented method of claim 1, wherein the first trained function and the second trained function are trained as a Markov decision process using policy gradients.

10. The computer-implemented method of claim 1, wherein the first trained function and the second trained function are reinforcement machine-learnt networks.

11. The computer-implemented method of claim 1, further comprising:
rendering an assistance image of the medical image data, and
displaying the assistance image with landmark locations of the second set of anatomic landmarks being highlighted.

12. The computer-implemented method of claim 1, further comprising:
generating the first representation from the medical image data by sampling the medical image data at the first resolution.

13. The computer-implemented method of claim 1, further comprising:
generating the second representation from the medical image data by sampling the medical image data at the second resolution, the second resolution being lower than or equal to an intrinsic resolution of the medical image data.

14. The computer-implemented method of claim 13, wherein the second resolution is preset, selected by a user from the set of one or more resolutions, or selected by a fourth trained function from the set of one or more resolutions.

15. A non-transitory computer program product storing program elements, to induce a computing unit of a system for detecting one or more anatomic landmarks in medical image data to perform the method of claim 1, when the program elements are loaded into a memory of, and executed by, the computing unit.

16. A non-transitory computer-readable medium storing program elements, readable and executable by a computing unit of a system for detecting one or more anatomic landmarks in medical image data, to perform the method of claim 1 when the program elements are executed by the computing unit.

17. The computer-implemented method of claim 1, wherein at least one of
the changing the position of the one or more first sub-spaces by at least one pixel includes adjusting the one or more first subspaces at least one of front, back, upwards, downwards, left, or right with respect to the medical image data, or
the changing the position of the one or more second sub-spaces by at least one pixel includes adjusting the one or more second subspaces at least one of front, back upwards, downwards, left, or right with respect to the medical image data.

18. The computer-implemented method of claim 1, wherein at least one of
the changing the position of the one or more first sub-spaces by at least one pixel includes rotating the one or more first sub-spaces around an axis, or
the changing the position of the one or more second sub-spaces by at least one pixel includes rotating the one or more first sub-spaces around an axis.

19. The computer-implemented method of claim 1, wherein the second resolution is selected by a fourth trained function from the set of one or more resolutions and the second trained function corresponds to the second resolution and is selected from the set of trained functions corresponding to each resolution of the set of resolutions.

20. A system for detecting one or more anatomic landmarks in medical image data, comprising:
an interface configured to receive medical image data depicting a body part of a patient;
a memory storing a first trained function trained to identify a set of anatomic landmarks in a representation of the medical image data at a first resolution, and a second trained function trained to identify a set of landmarks in a representation of the medical image data at a second resolution, the second trained function being different than the first trained function and the second resolution being higher than the first resolution; and
a processor configured to
apply the first trained function to a first representation of the medical image data at the first resolution to identify a first set of anatomic landmarks,
input the first set of anatomic landmarks to the second trained function,
apply the second trained function to a second representation of the medical image data at the second resolution, to identify a second set of anatomic landmarks using the first set of anatomic landmarks,
apply the first trained function to define one or more first sub-spaces in the first representation and specify sequences of actions based on a learned policy to reposition the one or more first sub-spaces in the first representation to parse the first representation to determine the first set of anatomic landmarks in one or more iterations of repositioning the one or more first subspaces, and apply the second trained function to define one or more second subspaces in the second representation based on landmark locations of the first set of anatomic landmarks and specify sequences of actions based on a learned policy to reposition the one or more second sub-spaces in the second representation to parse the second representation to determine the second set of anatomic landmarks in one or more iterations of repositioning the one or more second sub-spaces, wherein an action of the sequences of actions based on the learned policy of the first trained function includes changing a position of the one or more first sub-spaces by at least one pixel, an action of the sequences of actions based on the learned policy of the second trained function includes changing a position of the one or more second sub-spaces by at least one pixel, the first resolution is selected from a set of one or more resolutions by a third trained function based on an intrinsic resolution of the medical image data, the first resolution is lower than the intrinsic resolution of the medical image data, and the first trained function corresponds to the first resolution and is selected from a set of trained functions corresponding to each resolution of the set of resolutions.

21. The system of claim 20, wherein the second trained function is configured to define one or more of the second sub-spaces based on landmark locations of the first set of anatomic landmarks.

* * * * *